US007989467B2

(12) United States Patent
Tazi et al.

(10) Patent No.: US 7,989,467 B2
(45) Date of Patent: Aug. 2, 2011

(54) USE OF INDOLE-DERIVED COMPOUNDS FOR THE PREPARATION OF A MEDICAMENT THAT CAN BE USED TO TREAT DISEASES RELATED TO THE SPLICING PROCESS

(75) Inventors: Jamal Tazi, Clapiers (FR); Johann Soret, Teyran (FR); Philippe Jeanteur, Montferrier (FR); David Grierson, Versailles (FR); Christian Rivalle, Paris (FR); Emile Bisagni, Orsay (FR); Chi Hung Nguyen, Antony (FR)

(73) Assignees: Centre National de la Recherche Scientifique (CNRS) (FR); Universite Montpellier II (FR); Institut Curie (FR)

( * ) Notice: Subject to any disclaimer, the term of this patent is extended or adjusted under 35 U.S.C. 154(b) by 1503 days.

(21) Appl. No.: 10/570,849

(22) PCT Filed: Sep. 6, 2004

(86) PCT No.: PCT/FR2004/002261
§ 371 (c)(1),
(2), (4) Date: Sep. 6, 2004

(87) PCT Pub. No.: WO2005/023255
PCT Pub. Date: Mar. 17, 2005

(65) Prior Publication Data
US 2007/0054905 A1 Mar. 8, 2007

(30) Foreign Application Priority Data

Sep. 4, 2003 (FR) ..................................... 03 10460
Feb. 2, 2004 (FR) ..................................... 04 00973

(51) Int. Cl.
*A61K 31/44* (2006.01)
*C07D 211/68* (2006.01)
(52) U.S. Cl. ........................................ 514/284; 546/285
(58) Field of Classification Search .................. 546/285; 514/284
See application file for complete search history.

(56) References Cited

U.S. PATENT DOCUMENTS 6,162,811 A * 12/2000 Guillonneau et al. ........ 514/285
2002/0018768 A1 2/2002 Kerem

FOREIGN PATENT DOCUMENTS

| EP | 0 010 029 | 4/1980 |
| EP | 0 317 416 | 5/1989 |
| EP | 0394112 | 10/1990 |
| FR | 2387229 | 11/1978 |
| FR | 2485537 | 12/1981 |
| FR | 2627493 | 8/1989 |
| FR | 2 665 162 | 1/1992 |
| JP | 5-310736 | 11/1993 |
| WO | 92/09602 | 6/1992 |
| WO | 01/66129 | 9/2001 |

OTHER PUBLICATIONS

Chermann et al., 1978, CAS: 89:36630.*
Tazi J et al: "DNA topoisomerase I: customs officer at the border between DNA and RNA worlds?" Journal of Molecular Medicine (Berlin, Germany) Nov.-Dec. 1997 vol. 75, No. 11-12, Nov. 1997, pp. 786-800.
Poddevin B et al: "Dual Topoisomerase I and II Inhibition by Intoplicine (RP-60475), A New Antitumor Agent in Early Clinical Trials" Molecular Pharmacology, Baltimore, MD, US, vol. 44, No. 4, Oct. 1, 1993, pp. 767-774.
Pilch B et al: "Specific inhibition of serine- and arginine-rich splicing factors phosphorylation, spliceosome assembly, and splicing by the antitumor drug NB-506" Cancer Research Sep. 15, 2001 United States, vol. 61, No. 18, Sep. 15, 2001, pp. 6876-6884.
Snyder A L et al: "Inhibition of the Processing of Ribosomal Precursor RNA by Ntercalating Agents" Journal of Molecular Biology, vol. 58, No. 2, 1971, pp. 555-565.
Kennedy G D et al: "Preparation and Nucleic Acid Binding of Ellipticine Derivatives" Heterocyclic Communications, Freund Publishing House, Tel Aviv, IL, vol. 2, No. 2, 1996, pp. 125-128.
Peng Yanhua et al: "Rescue of mutant p53 transcription function by ellipticine." Oncogene, vol. 22, No. 29, Jul. 17, 2003, pp. 4478-4487.
Kansal V K et al: "The Biogenetic Synthetic and Biochemical Aspects of Ellipticine an Antitumor Alkaloid" Tetrahedron, vol. 42, No. 9, 1986, pp. 2389-2408.
Ohashi M et al: "Ellipticine and related anticancer agents" Expert Opinion on Therapeutic Patents 1996 United Kingdom, vol. 6, No. 12, 1996, pp. 1285-1294.
Pindur et al., "Antitumor active drugs as intercalators of deooxyribonucleic acid molecular models of intercalaton complexes", Journal of Chemical Education, vol. 70, No. 4, (1993).
Hagg et al, Induction of Endoplasmic Reticulum stress by Elliptiicine Plant Alkaloids, Molecular Cancer Therapeutics, 3(4);489-497 (2004).
Sharp, P.A. (1994). Split genes and RNA splicing. Cell 77, 805-815).
Manley, J.L. and Tacke, R. (1996). SR proteins and splicing control. Genes Dev. 10, 1569-1579.
Graveley, B.R. Sorting out the complexity of SR protein functions. RNA.2000. 6, 1197-1211.
Wang, H.Y. et al., SC35 plays a role in T cell development and alternative splicing of CD45. Mol.Cell 2001.7, 331-342.
Ewing, B. and Green, P. Analysis of expressed sequence tags indicates 35,000 human genes. Nat.Genet.2000. 25, 232-234.

(Continued)

*Primary Examiner* — Rei-tsang Shiao
(74) *Attorney, Agent, or Firm* — Lerner, David, Littenberg, Krumholz & Mentlik, LLP

(57) ABSTRACT

The invention relates to indole-derived compounds and to the use of said compounds for the preparation of a medicament that can be used to treat diseases related to the process of splicing pre-messenger RNAs in the cell, such as Frasier syndrome, frontotemporal dementia linked to chromosome 17 (a form of Parkinson's disease), Leigh syndrome (a type of encephalopathy), atypical cystic fibrosis, certain neuropathologies including Alzheimer's disease linked to a mutation in the Tau protein, muscle atorphy which affects the SMN (Survival of Motor Neuron) gene, depression linked to a serotonin splicing impairment, and certain cancers in which the global splicing process is affected (e.g. breast cancer, colon cancer and certain lymphomas), as well as viral diseases such as AIDS.

13 Claims, 6 Drawing Sheets

OTHER PUBLICATIONS

Cartegni, L. et al., Listening to silence and understanding nonsense: exonic mutations that affect splicing. Nat.Rev. Genet.2002. 3, 285-298.

Nissim-Rafinia, M. et al., Cellular and viral splicing factors can modify the splicing pattern of CFTR transcripts carrying splicing mutations. Hum.Mol.Genet.2000. 9, 1771-1778.

Sazani, P. et al., Systemically delivered antisense oligomers upregulate gene expression in mouse tissues. Nat. Biotechnol.2002. 20, 1228-1233.

Cartegni, L. et al., Correction of disease-associated exon skipping by synthetic exon-specific activators. Nat.Struct. Biol.2003. 10, 120-125.

Andreassi, C. et al., Aclarubicin treatment restores SMN levels to cells derived from type I spinal muscular atrophy patients. Hum.Mol. Genet.2001.10, 2841-2849.

Liu, X et al., Partial correction of endogenous DeltaF508 CFTR in human cystic . fibrosis airway epithelia by spliceosome-mediated RNA trans-splicing. Nat.Biotechnol. 2002. 20, 47-52.

Uekama, K. et al., Cyclodextrins in drug carrier systems. Crit.Rev. Ther.Drug Carrier.Syst. 1987. 3, 1-40.

Prochiantz, A., Getting hydrophilic compounds into cells: lessons from homeopeptides. Curr.Opin.Neurobiol. 1996. 6, 629-634.

et Vives, E. et al., A truncated HIV-1 Tat protein basic domain rapidly translocates through the plasma membrane and accumulates in the cell nucleus. J.Biol.Chem. 1997. 272, 16010-16017.

Douglas, S.J. et al., Nanoparticles in drug delivery. Crit.Rev.Ther. Drug Carrier.Syst. 1987. 3, 233-261 Gregoriadis, G. et al., Liposomes in drug delivery. Clinical, diagnostic and ophthalmic potential. Drugs 1993. 45, 15-28.

Black, D.L., Mechanisms of Alternative Pre-Messenger RNA Splicing. Annu.Rev.Biochem.2003. 72,291-336.

Gregoriadis, G. et al., Liposomes in drug delivery. Clinical, diagnostic and ophthalmic potential. Drugs 1993. 45, 15-28.

Hofmann, Y. et al., Htra2-beta 1 stimulates an exonic splicing enhancer and can restore full-length SMN expression to survival motor neuron 2 (SMN2). Proc.Natl.Acad.Sci.U.S.A.2000. 97, 9618-9623.

Sazani, P. and Kole, R. Modulation of alternative splicing by antisense oligonucleotides. Prog.Mol.Subcell.Biol.2003. 31, 217-239.

Caputi et al., 2004. A bidirectional SF2/ASF- and SRp40-dependent splicing enhancer regulates human immunodeficiency virus type 1 rev, env, vpu, and nef gene expression. J. Virol. 78: 6517-26.

Pongoski et al., 2002. Positive and negative modulation of human immunodeficiency virus type 1 Rev function by cis and trans regulators of viral RNA splicing. J. Virol. 76: 5108-20.

Folks et al., 1988. Characterization of a promonocyte clone chronically infected with HIV and inducible by 13-phorbol-12-myristate acetate. J. Immunol., 140: 1117-1122.

Jacquenet et al., 2001, A second exon splicing silencer within human immunodeficiency virus type 1 tat exon 2 represses splicing of Tat mRNA and binds protein hnRNP. H. J. Biol. Chem. 276: 40464-75.

Chermann et al,. Current Chemotherapy: Proceedings of the 10th International Congress of Chemotherapy (vol. II), pp. 1200-1201 (1978).

\* cited by examiner

USE OF INDOLE-DERIVED COMPOUNDS FOR THE PREPARATION OF A MEDICAMENT THAT CAN BE USED TO TREAT DISEASES RELATED TO THE SPLICING PROCESS

CROSS-REFERENCE TO RELATED APPLICATIONS

The present application is a national phase entry under 35 U.S.C. §371 of International Application No. PCT/FR2004/002261 filed Sep. 6, 2004, published in France, which claims priority from French Patent Application No. 0310460 filed Sep. 4, 2003 and French Patent Application No. 0400973 filed Feb. 2, 2004, all of which are incorporated herein by reference.

BACKGROUND OF THE INVENTION

The invention relates to novel indole-derived compounds and their use in the preparation of a medicine of use in the treatment of diseases related to the splicing process.

Certain indole-derived compounds, such as ellipticine and aza-ellipticine derivatives, are already known as intercalating molecules which correct errors in genetic expression during the replication process. They have been more specifically described for the treatment of diseases such as cancer, leukemia and AIDS (FR 2 627 493, FR 2 645 861, FR 2 436 786).

The intracellular splicing process consists of eliminating pre-messenger RNA introns in order to produce mature RNA messengers which can be used by the cell's translation machinery (Sharp, P. A. (1994). Split genes and RNA splicing. Cell 77, 805-815). In the case of alternative splicing, the same precursor can be the source for messenger RNAs that code for functionally-distinct proteins (Black, D. L. Mechanisms of Alternative Pre-Messenger RNA Splicing. Annu. Rev. Biochem. 2003. 72, 291-336). The precise selection of the 5' and 3' splice sites is thus a mechanism which generates diversity and which can lead to the regulation of gene expression as a function of tissue type and over the course of an organism's development. The factors implicated in this selection include a family of proteins termed SR (serine/arginine-rich protein) characterized by the presence of one or two RRM (RNA-recognition motif) RNA-binding domains and a domain termed RS (arginine/serine) rich in arginine and serine residues (Manley, J. L. and Tacke, R. (1996). SR proteins and splicing control. Genes Dev. 10, 1569-1579). By binding to the pre-mRNA's short exonic and intronic sequences, termed ESE (exonic splicing enhancer) and ISE (intronic splicing enhancer), SR proteins are capable of dose-dependently activating suboptimal splicing sites and enabling the inclusion of exons (Graveley, B. R. Sorting out the complexity of SR protein functions. RNA. 2000. 6, 1197-1211). SR protein activity in alternative splicing is specific insofar as the inactivation of the corresponding gene is lethal (Wang, H. Y. et al., SC35 plays a role in T cell development and alternative splicing of CD45. Mol. Cell 2001. 7, 331-342).

Sequencing of the human genome and analysis of EST (expressed sequence tag) collections has revealed that 35 to 65% of genes are expressed in the form of alternative splicing variants (Ewing, B. and Green, P. Analysis of expressed sequence tags indicates 35,000 human genes. Nat. Genet. 2000. 25, 232-234). This mechanism is thus a favored target of modifications which can affect the factors implicated in the regulation of splicing and of mutations which affect the sequences necessary to this regulation. At present, it is estimated that approximately 50% of the point mutations responsible for genetic diseases result in splicing errors. These mutations can interfere with splicing by inactivating or creating splicing sites, but also by modifying or generating regulation elements known as "splicing enhancers" and "splicing silencer" in a specific gene (Cartegni, L. et al., Listening to silence and understanding nonsense: exonic mutations that affect splicing. Nat. Rev. Genet. 2002. 3, 285-298).

The strategies currently developed to correct these splicing errors are based on the use of various types of molecules.

The document by Tazi J et al. (DNA topoisomerase I: customs officer at the border between DNA and RNA worlds?, Journal of Molecular Medecine (Berlin, Germany) 1997 November-December, vol. 75, no. 11-12) describes that certain derivatives inhibit DNA topoisomerase I, a specific kinase which phosphorylates SR splicing factors.

The document by Poddevin B et al. (Dual topoisomerase I and II inhibition by intoplicine (RP-60475), a new antitumor agent in early clinical trials, Molecular Pharmacology, Baltimore, Md., US, vol. 44, no. 4) describes that intoplicine is a molecule that inhibits both topoisomerase I and topoisomerase II, demonstrating that this compound can be active against tumors.

The document by Pilch B et al. (Specific inhibition of serine- and arginine-rich splicing factors, phosphorylation, spliceosome assembly, and splicing by the antitumor drug NB-506, Cancer Research, 15 Sep. 2001, US, vol. 61, no. 18) describes that indolocarbazole medicines inhibit topoisomerase I and can as a result be considered anti-cancer medicines.

One strategy targeting the development of new molecules that make it possible to correct or eliminate splicing errors, for example, is based on the overexpression of proteins that interfere with this type of splicing (Nissim-Rafinia, M. et al., Cellular and viral splicing factors can modify the splicing pattern of CFTR transcripts carrying splicing mutations. Hum. Mol. Genet. 2000. 9, 1771-1778; Hofmann, Y. et al., Htra2-beta 1 stimulates an exonic splicing enhancer and can restore full-length SMN expression to survival motor neuron 2 (SMN2). Proc. Natl. Acad. Sci. U.S.A. 2000. 97, 9618-9623).

Another strategy is based on the use of antisense oligonucleotides (Sazani, P. et al., Systemically delivered antisense oligomers upregulate gene expression in mouse tissues. Nat. Biotechnol. 2002. 20, 1228-1233; Sazani, P. and Kole, R. Modulation of alternative splicing by antisense oligonucleotides. Prog. Mol. Subcell. Biol. 2003. 31, 217-239) and of PNA (peptidic nucleic acid) (Cartegni, L. et al., Correction of disease-associated exon skipping by synthetic exon-specific activators. Nat. Struct. Biol. 2003. 10, 120-125) making it possible to inhibit or activate, respectively, a splicing event.

Still another strategy is based on the identification of compounds that influence the effectiveness of splicing of the pre-mRNA of interest (Andreassi, C. et al., Aclarubicin treatment restores SMN levels to cells derived from type I spinal muscular atrophy patients. Hum. Mol. Genet. 2001. 10, 2841-2849).

Finally, a strategy based on the use of trans-splicing to replace mutated exons has been described (Liu, X. et al., Partial correction of endogenous DeltaF508 CFTR in human cystic fibrosis airway epithelia by spliceosome-mediated RNA trans-splicing. Nat. Biotechnol. 2002. 20, 47-52).

One of the disadvantages of the strategies developed and cited above to correct or eliminate splicing errors is their cost of production. Indeed, the cost of producing antisense oligonucleotides that must be modified to improve their stability, and also the cost of producing PNA molecules, is high.

Another disadvantage of the strategies developed and cited above is that they require the use of expression vectors, as for example for the strategy based on the use of trans-splicing.

SUMMARY OF THE INVENTION

The inventors sought to find a new strategy, in particular one that uses molecules capable of inhibiting pre-messenger RNA splicing processes and that does not present the disadvantages of the molecules of the prior art.

Thus the present invention relates to the use of indole-derived compounds such as derivatives of benzo-indole or pyrido-indole corresponding to the following formula I:

Formula I when ring A is in position b: X represents N or CR4 or N⁺R4 anhydro base
and cycle A corresponds to when cycle A is in position a or c: X represents N
and cycle A corresponds to in which: R1 represents:
  an atom of hydrogen or halogen or a —C═N—OH or —O—C(═O)(CH₃) or —C≡N group, or
  a —N—R6R7 group,
where R6 and R7 represent independently of one another:
  a hydrogen atom,
  a ring at C6, saturated or unsaturated, possibly containing an atom of nitrogen and possibly substituted by one or more alkyl groups at C1 to C3, or
  a linear, branched and/or unsaturated alkyl group at C1 to C13 in which one or more atoms of carbon can be substituted by an atom of nitrogen, the aforementioned alkyl group being possibly substituted by one or more —OH and/or ═O groups and/or by a group such as:

the aforementioned group being possibly substituted by an alkyl group at C1 to C3 which itself is possibly substituted by an amino group,
  a —NH—R8 group
    where R8 represents an alkyl-N—R9R10 group
      where the alkyl group represents a linear or branched group at C1 to C13 possibly unsaturated and/or substituted by one or more alkyl groups at C1 to C3 and/or hydroxyl groups,
      R9 and R10 represent independently of one another a hydrogen atom or an alkyl group at C1 to C4 possibly substituted by one or more hydroxyl and/or oxo groups,
R2 represents a hydrogen atom, a methyl group or a —NH—(CH₂)₃—N(CH₃)₂ group, or is absent when ring A is in position a,
R3 represents a hydrogen atom, a halogen atom or a methyl, amino or methoxymethyl group, or —NH—R8 such as defined previously,
R4 represents a hydrogen atom, a hydroxyl or alkyl group at C1-C6 or a methoxy group possibly substituted by a phenyl group,
R5 represents a hydrogen atom or a methyl or methoxymethyl group when X represents N or CR4 and R5 is absent when X represents N⁺R4 anhydro base,
Z represents a hydrogen atom or a hydroxyl or methoxy group or —O-alkyl-C═O(O-alkyl), with alkyl representing a group at C1-C6,
R11 and R12 represent independently of one another a hydrogen atom or an alkyl group at C1-C3, and R11 is absent when ring A is in position c,
R13 represents a hydrogen atom or a methyl group, and the pharmaceutically acceptable salts of the aforementioned compounds, their isomers and/or mixtures,
for the preparation of a medication for the treatment of diseases related to pre-messenger RNA splicing processes within the cell.

(B) Analysis of the splicing products of M3S1-PDH pre-messenger RNA obtained in vitro in the presence of various compounds. The structure of the various splicing products is indicated. The line represents the introns and the rectangles represent the three exons.

Figure 5:
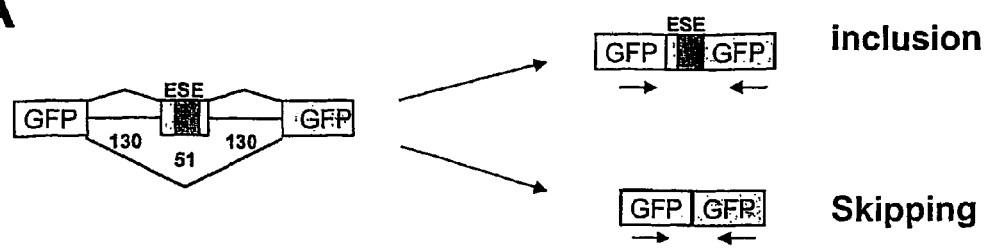
Figure 5:
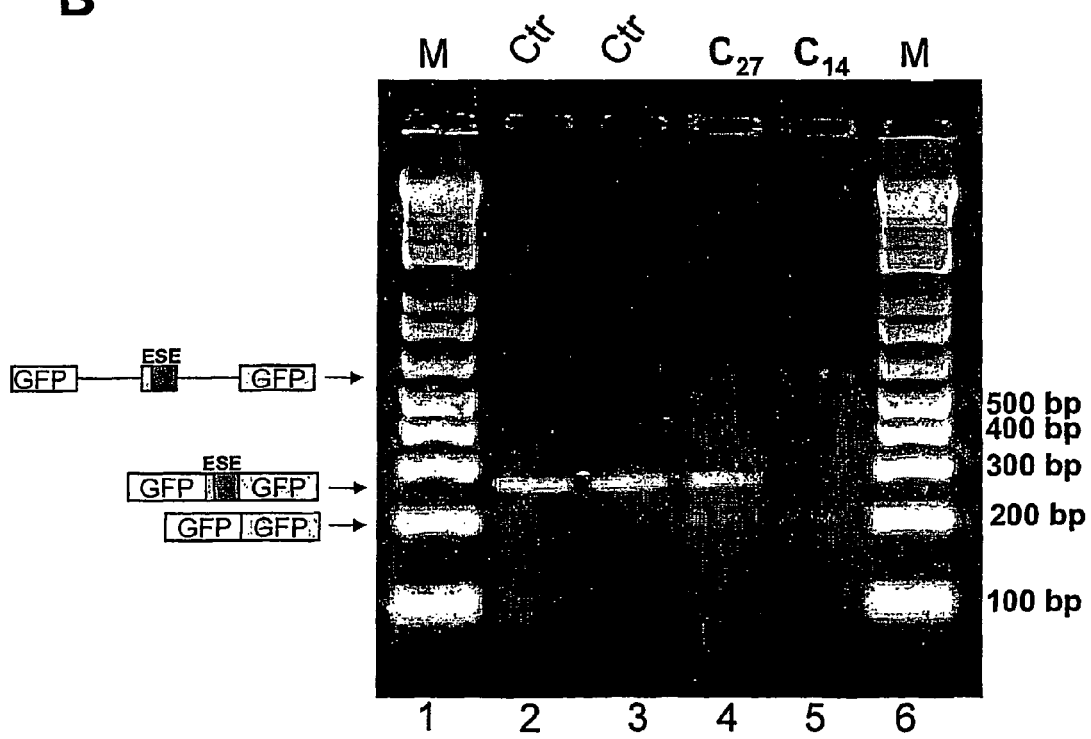

FIG. 5: (A) Structure of the transgene and the two types of transcripts produced by alternative splicing. The arrows indicate the position of the primers used for the PCR.

(B) Analysis of the PCR products on 2% agarose gel. M indicates the DNA markers corresponding to multiples of 100 base pairs (lanes 1 and 6). PCRs were performed on RNAs arising from untreated cells (lanes 2 and 3), from cells treated by 1 µM of compound $C_{27}$ (lane 4) and by 1 µM of compound $C_{14}$ (lane 5).

Figure 6:
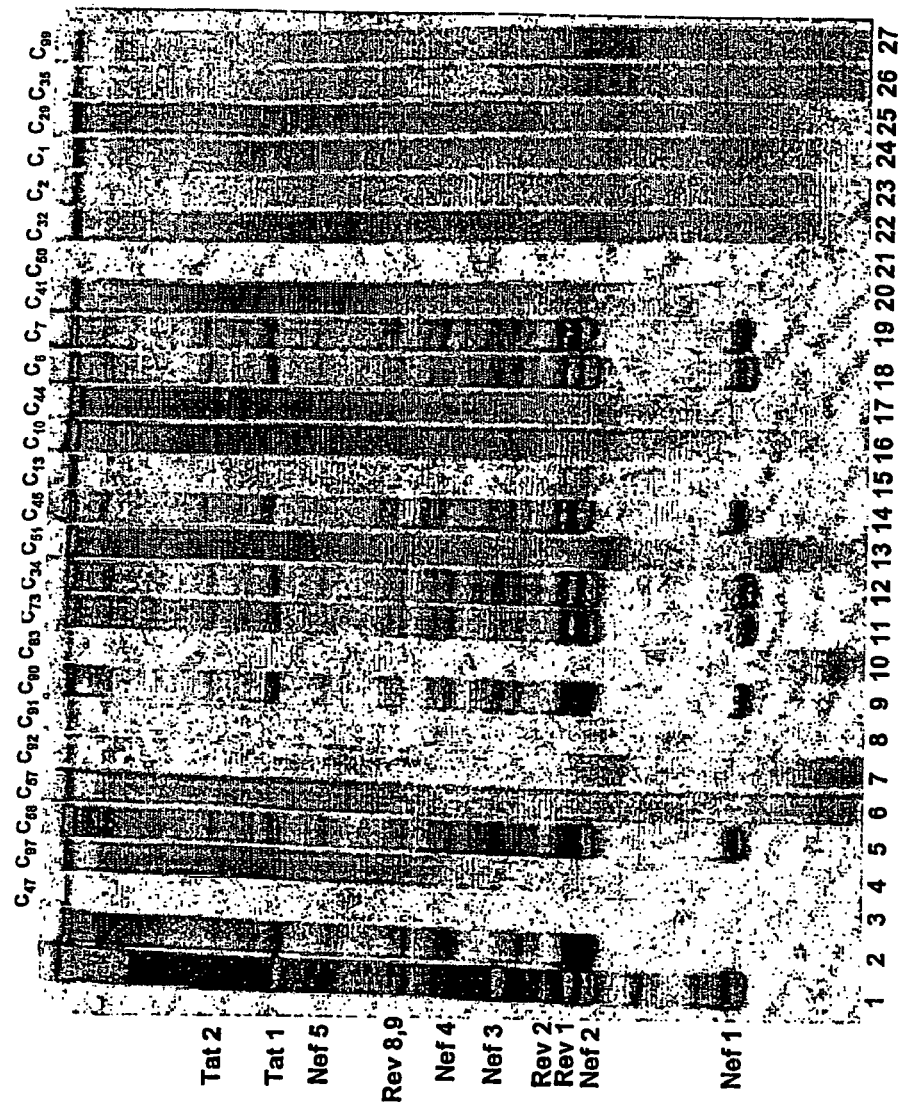

FIG. 6: Analysis of RT-PCR amplification products from viral mRNAs arising from U1 cells stimulated by PMA (lanes 1, 3-27) in the absence (lane 1) or presence (lanes 3-27) of the various compounds. Lane 2 represents amplification products from cells not stimulated by PMA. The RT-PCR nomenclature is in agreement with Purcell D. F. and Martin M. A. (1993, Alternative splicing of human immunodeficiency virus type 1 mRNA modulates viral protein expression, replication, and infectivity. J Virol. 67:6365-78).

DETAILED DESCRIPTION

By "diseases related to pre-messenger RNA splicing processes within the cell" is meant all the diseases related to the splicing process, which is to say, diseases caused by splicing-process modifications and diseases whose appearance requires that cellular splicing processes are activated. Meant in particular are genetic diseases resulting from splicing-process modification such as for example Frasier syndrome, frontotemporal dementia related to chromosome 17 (a form of Parkinson's), Leigh syndrome (a type of encephalopathy), atypical cystic fibrosis, certain neuropathologies, such as in particular Alzheimer's, related to Tau protein mutation, amyotrophy that influences the SMN (survival of motor neuron) gene, depression related to disturbances in serotonin splicing and certain cancers in which the overall splicing process is affected (notably breast cancer, colon cancer and certain lymphomas).

Equally meant are diseases of viral origin or due to the intrusion of a virus into a human or animal, termed viral diseases, for which ESE sequences are identified. AIDS, whose ESE sequences are identified in the splicing of certain pre-messenger RNA of key genes implicated in the replication of the virus responsible for AIDS, can be cited in particular.

By "atom of halogen" is meant the group F, Cl, Br and I, and more particularly Cl.

By "anhydro base" is meant a compound resulting from acid-base neutralization (with loss of water) of iminium hydroxides containing an acid site conjugated with the iminium function (see IUPAC). In the case of the present invention, hydroxide is replaced by amino in the anhydro base.

The first advantage related to the use of indole derivatives such as benzo-indole or pyrido-indole according to the invention to treat diseases related to the splicing process is of a financial nature. Indeed, the cost of production of these molecules is much lower than that of antisense oligonucleotides or of PNA hybrid molecules.

The second advantage of indole derivatives according to the invention is related to their ease of administration and the fact that this treatment strategy does not require the use of expression vectors.

Penetration of the molecules according to the invention into the cells and their targeting towards specific tissues can be carried out either by using polymers (Uekama, K. et al., Cyclodextrins in drug carrier systems.

Crit. Rev. Ther. Drug Carrier. Syst. 1987. 3, 1-40), by using vectors such as peptides and lipids (Prochiantz, A., Getting hydrophilic compounds into cells: lessons from homeopeptides. Curr. Opin. Neurobiol. 1996. 6, 629-634 et Vives, E. et al., A truncated HIV-1 Tat protein basic domain rapidly translocates through the plasma membrane and accumulates in the cell nucleus. J. Biol. Chem. 1997. 272, 16010-16017) or by using particles such as nanoparticles and liposomes (Douglas, S. J. et al., Nanoparticles in drug delivery. Crit. Rev. Ther. Drug Carrier. Syst. 1987. 3, 233-261 and Gregoriadis, G. et al., Liposomes in drug delivery. Clinical, diagnostic and ophthalmic potential. Drugs 1993. 45, 15-28).

In a preferred embodiment, the benzo-indole derivatives are pyrido-carbazole derivatives, and in formula I, when X represents CR4, ring A represents

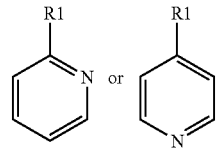

R1 represents a —N—R6R7 or —NH—R8 group, a hydrogen atom, a —C=N—OH or —O—C(=O)(CH₃) or —C≡N group,
R3 represents a hydrogen atom,
R4 represents a hydroxy group or a methoxy group possibly substituted by a phenyl group,
R13 represents a hydrogen atom, and
R2, R5, R6, R7, R8, R9, R10, R11 and R12 are such as defined previously.

In another preferred embodiment, the pyrido-indole derivatives are derivatives of pyrido-pyrrolo-isoquinoline (or quinoline) and in formula I, when X represents N or N⁺R4 anhydro base, ring A represents

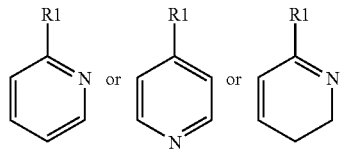

R1 represents a halogen atom, an amino group, —N—R₆R₇ or —NH—R8,
R2 represents a hydrogen atom or a methyl group,
R3 represents a hydrogen atom or a NH—R8 group,
R4 represents a hydrogen atom or a methyl group, R5 represents a hydrogen atom or a methyl group when X represents N and R5 is absent when X represents N⁺R4 anhydro base,
R11 represents a hydrogen atom or a methyl group, and
R6, R7, R8, R9, R10, R12 and R13 are such as previously defined.

In still another preferred embodiment, the pyrido-indole derivatives are derivatives of benzo-pyrido-indole and in formula I, when X represents N, ring A represents

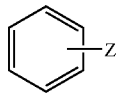

and is in position a, b or c,
R3 represents a halogen atom, an amino group, a —N—R6R7 or —NH—R8 group,
R5 represents a hydrogen atom or a methyl group,
R2 and R11 represent a hydrogen atom or a methyl group, or are respectively absent when ring A is in position a and c,
R13 represents a hydrogen atom, and
Z, R6, R7, R8, R9, R10 and R12 are such as previously defined.

The preferred compounds are:
N'-(9-methoxy-5,6,11-trimethyl-6H-pyrido[4,3-b]carbazol-1-yl)-N,N-dimethyl-propane-1,3-diamine,
N'-(9-methoxy-6,11-dimethyl-6H-pyrido[4,3-b]carbazol-1-yl)-N,N-dimethyl-propane-1,3-diamine,
10-chloro-2,6-dimethyl-2H-pyrido[3',4':4,5]pyrrolo[2,3-g]isoquinoline,
9-hydroxy-5-methyl-6H-pyrido[4,3-b]carbazol-1-yl acetic acid ester,
1-(3-dimethylamino-propylamino)5-methyl-6H-pyrido[4,3-b]carbazol-9-ol,
9-methoxy-5-methyl-6H-pyrido[4,3-b]carbazol-1-carbaldehyde oxime,
N'(9-methoxy-5-methyl-6H-pyrido[4,3-b]carbazol-11-yl)-N,N-dimethyl-propane-1,3-diamine,
N,N-diethyl-N'-(9-methoxy-5-methyl-6H-pyrido[4,3-b]carbazol-1-yl)-propane-1,3-diamine,
N'-(6,11-dimethyl-5H-pyrido[3',4':4,5]pyrrolo[2,3-g]isoquinolin-10-yl)-N,N-dimethyl-propane-1,3-diamine,
allyl-(9-methoxy-5,11-dimethyl-6H-pyrido[4,3-b]carbazol-1-yl)-amine,
N,N-diethyl-N4-(9-methoxy-5-methyl-6H-pyrido[4,3-b]carbazol-1-yl)-pentane-1,4-diamine,
N,N-dimethyl-N'-(6-methyl-5H-pyrido[3',4':4,5]pyrrolo[2,3-g]isoquinolin-10-yl)-propane-1,3-diamine,
9-methoxy-1-[6-(9-methoxy-5-methyl-6H-pyrido[4,3-b]carbazol-1-ylamino)-hexylamino]-2,5-dimethyl-6H-pyrido[4,3-b]carbazol-2-ium iodide,
{3-[4(3-amino-propyl)-piperazin-1-yl]-propyl}-9-methoxy-5-methyl-6H-pyrido[4,3-b]carbazol-1-yl)-amine,
(3-imidazol-1-yl-propyl)-9-methoxy-5-methyl-6H-pyrido[4,3-b]carbazol-1-yl)-amine,
(9-methoxy-5-methyl-6H-pyrido[4,3-b]carbazol-1-yl)-(2,2,6,6-tetramethyl-piperidin-4-yl)-amine,
N-ethyl-N-[3-(9-methoxy-5,11-dimethyl-6H-pyrido[4,3-b]carbazol-1-ylamino)-propyl]-succinamic acid,
N-ethyl-N-[3-(6-methyl-5H-pyrido[3',4':4,5]pyrrolo[2,3-g]isoquinolin-10-ylamino)-propyl]-succinamic acid,
5,11-dimethyl-1-(3-methyl-butylamino)-6H-pyrido[4,3-b]carbazol-9-ol,
2-{(2-hydroxy-ethyl)-[3-(6-methyl-5H-pyrido[3',4':4,5]pyrrolo[2,3-g]isoquinolin-10-ylamino}propyl]-amino-ethanol,
N,N-diethyl-N'-(6-methyl-5H-pyrido[3',4':4,5]pyrrolo[2,3-g]isoquinolin-10-yl)-ethane-1,2-diamine,
N'-(9-benzyloxy-6-methoxymethyl-5-methyl-6H-pyrido[4,3-b]carbazol-1-yl)-N,N-diethyl-propane-1,3-diamine,
1-(3-diethylamino-propylamino)-6-methoxymethyl-5-methyl-6H-pyrido[4,3-b]carbazol-9-ol,
9-methoxy-5-methyl-4,6-dihydro-3H-pyrido[4,3-b]carbazol,
N-(6-methyl-5H-pyrido[3',4':4,5]pyrrolo[2,3-g]isoquinolin-10-yl)-propane-1,3-diamine,
1-(3-diethylamino-propylamino)-5,11-dimethyl-6H-pyrido[4,3-b]carbazol-9-ol,
N-(9-methoxy-5,11-dimethyl-6H-pyrido[4,3-b]carbazol-1-yl)-propane-1,3-diamine,
N-3-(5,6-dimethyl-5H-pyrido[3',4':4,5]pyrrolo[2,3-g]isoquinolin-10-yl)-N, N-1-diethyl-butane-1,3-diamine,
N,N-diethyl-N'-(9-methoxy-5,6,11-trimethyl-6H-pyrido[4,3-b]carbazol-1-yl)-ethane-1,2-diamine,
N-(6,11-dimethyl-5H-pyrido[3',4':4,5]pyrrolo[2,3-g]isoquinolin-10-yl)-N'-ethyl-propane-1,3-diamine,
N-(9-methoxy-5-methyl-6H-pyrido[4,3-b]carbazol-1-yl)-propane-1,3-diamine,
N'-(5,6-dimethyl-5H-pyrido[3'4':4,5]pyrrolo[2,3-g]isoquinolin-10-yl)-N,N-dimethyl-propane-1,3-diamine,
N-(5,6-dimethyl-5H-pyrido[3',4':4,5]pyrrolo[2,3-g]isoquinolin-10-yl)-N'-ethyl-propane-1,3-diamine,
9-methoxy-5-methyl-6H-pyrido[4,3-b]carbazol-1-carbonitrile,
1-(3-diethylamino-propylamino)-5-methyl-6H-pyrido[4,3-b]carbazol-9-ol,
(9-methoxy-5,11-dimethyl-6H-pyrido[4,3-b]carbazol-1-yl)-(3-morpholin-4-yl-propyl)-amine,
N-ethyl-N'-(9-methoxy-5-methyl-6H-pyrido[4,3-b]carbazol-1-yl)-propane-1,3-diamine,
N-(9-methoxy-5-methyl-6H-pyrido[4,3-b]carbazol-1-yl)-pentane-1,5-diamine,
N-(9-methoxy-5-methyl-6H-pyrido[4,3-b]carbazol-1-yl)-hexane-1,6-diamine,
N'-(9-methoxy-5-methyl-6H-pyrido[4,3-b]carbazol-1-yl)-N,N-dimethyl-ethane-1,2-diamine,
N,N-diethyl-N'-(9-methoxy-5,11-dimethyl-6H-pyrido[4,3-b]carbazol-1-yl)-propane-1,3-diamine,
(9-methoxy-5-methyl-6H-pyrido[4,3-b]carbazol-1-yl)-(2-pyrrolidin-1-yl-ethyl)-amine,
3-(9-methoxy-5-methyl-6H-pyrido[4,3-b]carbazol-1-ylamino)-propane-1,2-diol,
1-diethylamino-3-(9-methoxy-5-methyl-6H-pyrido[4,3-b]carbazol-1-ylamino)-propan-2-ol,
(3-imidazol-1-yl-propyl)-(6-methyl-5H-pyrido[3',4':4,5]pyrrolo[2,3-g]isoquinolin-10-yl)-amine,
decyl-(9-methoxy-5,11-dimethyl-6H-pyrido[4,3-b]carbazol-1-yl)-amine,
N-(3-methoxy-10-methyl-11H-benzo[g]pyrido[4,3-b]indol-7-yl)-butane-1,4-diamine,
8-methyl-11-(3-methylamino-propylammo)-7H-benzo[e]pyrido[4,3-b]indol-3-ol,
1-diethylamino-3-(9-methoxy-5,11-dimethyl-6H-pyrido[4,3-b]carbazol-1-ylamino)-propan-2-ol,
N,N-diethyl-N'-(9-methoxy-5,6-dimethyl-6H-pyrido[4,3-b]carbazol-1-yl)-ethane-1,2-diamine,
N-N,diethyl-N'-(6-methyl-5H-pyrido[3',4':4,5]pyrrolo[2,3-g]isoquinolin-10-yl)-propane-1,3-diamine, N-1,N-10-Bis-(3-diethylamino-propyl)-3,6-dimethyl-5H-pyrido[3',4':4,5]pyrrolo[2,3-g]isoquinoline-1,10-diamine,
N-ethyl-N'-(9-methoxy-5,11-dimethyl-6H-pyrido[4,3-b]carbazol-1-yl)-propane-1,3-diamine,
N-(5,6-dimethyl-5H-benzo[f]pyrido[4,3]indol-1-yl)-N'-ethyl-propane-1,3-diamine,
N'-(9-methoxy-5,6-dimethyl-5H-benzo[f]pyrido[4,3-b]indol-1-yl)-N,N-dimethyl-propane-1,3-diamine,
1-(3-dimethylamino-propylamino)-5,6-dimethyl-5H-benzo[f]pyrido[4,3-b]indol-9-ol,
N-(3-methoxy-8-methyl-7H-benzo[e]pyrido[4,3-b]indol-11-yl)-N'-methyl-propane-1,3-diamine,
5-(7-chloro-10-methyl-11H-benzo[g]pyrido[4,3-b]indol-3-yloxy)-pentanoic acid ethyl ester,
N,N-dimethyl-N'-(10,11-dimethyl-10H-pyrido[3',4':4,5]pyrrolo[3,2-g]quinoline)4-yl-propane-1,3-diamine,
N,N-diethyl-N'-(10,11-dimethyl-10H-pyrido[3',4':4,5]pyrrolo[3,2-]quinoline)-4-yl-propane-1,3-diamine,
N'-(7-methoxy-10,11-dimethyl-10H-pyrido[2,3-b]carbazol-4-yl)-N,N-dimethyl-propane-1,3-diamine,
N,N-diethyl-N'-(7-methoxy-10,11-dimethyl-10H-pyrido[2,3-b]carbazol-4-yl)-propane-1,3-diamine,
9-methoxy-5,11-dimethyl-6H-pyrido[4,3-b]carbazol-1-yl-amine,
N,N-diethyl-N'-(7-methoxy-11-methyl-10H-pyrido[2,3-b]carbazol-4-yl)-propane-1,3-diamine,
N,N-diethyl-N'-(11-methyl-10H-pyrido[3',4':4,5]pyrrolo[3,2-g]quinoline)-4-yl-propane-1,3-diamine,
N,N-diethyl-N'-(7-methoxy-5,11-dimethyl-10H-pyrido[2,3-b]carbazol-4yl)-propane-1,3-diamine,
N,N-dimethyl-N'-(11-methyl-10H-pyrido[3',4':4,5]pyrrolo[3,2-g]quinoline)-4-yl-propane-1,3-diamine,
11-(3-dimethylamino-propylamino)-8-ethyl-7H-benzo[e]pyrido[4,3-b]indol-3-ol,
7-(3-diethylamino-propylamino)10,11-dimethyl-11H-benzo[g]pyrido[4,3-b]indol-4-ol,
11-(3-dimethylamino-propylamine)-7H-benzo[e]pyrido[4,3-b]indol-3-ol,
N'-(3-methoxy-7H-benzo[e]pyrido[4,3-b]indol-11-yl)-N,N-dimethyl-propane-1,3-diamine,
N'-8-ethyl-3-methoxy-7-methyl-7H-benzo[e]pyrido[4,3-b]indol-11-yl)-N,N-dimethyl-propane-1,3-diamine,
11-(3-dimethylamino-propylamino)-8-methyl-7H-benzo[e]pyrido[4,3-b]indol-2-ol,
N,N-diethyl-N'-(3-methoxy-10,11-dimethyl-11H-benzo[g]pyrido[4,3-b]indol-7-yl)-propane-1,3-diamine,
11-(3-dimethylamino-propylamino)-7,8-dimethyl-7H-benzo[e]pyrido[4,3-b]indol-3-ol,
7-(3-dimethylamino-propylamino)-10-methyl-11H-benzo[g]pyrido[4,3-b]indol-4-ol,
N'-(2-methoxy-8-methyl-7H-benzo[e]pyrido[4,3-b]indol-11-yl)-N,N-dimethyl-propane-1,3-diamine,
N'-(10,11-dimethyl-11H-benzo[g]pyrido[4,3-b]indol-7-yl)-N,N-diethyl-propane-1,3-diamine,
N'-(7,8-dimethyl-7H-benzo[e]pyrido[4,3-b]indol-11-yl)-N,N-dimethyl-propane-1,3-diamine,
N,N-dimethyl-N'-(10-methyl-11H-benzo[g]pyrido[4,3-b]indol-7-yl)-propane-1,3-diamine,
7-(3-diethylamino-propylamino)-10,11-dimethyl-11H-benzo[g]pyrido[4,3-b]indol-3-ol,
N,N-diethyl-N'-(10-methyl-11H-benzo[g]pyrido[4,3-b]indol-7-yl)-propane-1,3-diamine,
4-methoxy-10-methyl-11H-benzo[g]pyrido[4,3-b]indol-7-ylamine,
N,N-diethyl-N'-(3-methoxy-10-methyl-11H-benzo[g]pyrido[4,3-b]indol-7-yl)-propane-1,3-diamine,
N'-(4-methoxy-10,11-dimethyl-11H-benzo[g]pyrido[4,3-b]indol-7-yl)-N,N-dimethyl-propane-1,3-diamine,
7-(3-(dimethylamino-propylamino)-10,11-dimethyl-11H-benzo[g]pyrido[4,3-b]indol-4-ol,
N,N-dimethyl-N'-(8-methyl-7H-benzo[e]pyrido[4,3-b]indol-11-yl)-propane-1,3-diamine,
11-(3-dimethylamino-2-methyl-propylamino)-8-methyl-7H-benzo[e]pyrido[4,3-b]indol-3-ol,
N-(3-methoxy-8-methyl-7H-benzo[e]pyrido[4,3-b]indol-11-yl)-propane-1,3-diamine,
11-(3-amino-propylamino)-8-methyl-7H-benzo[e]pyrido[4,3-b]indol-3-ol,
N-(3-methoxy-10-methyl-11H-benzo[g]pyrido[4,3-b]indol-7-yl)-propane-1,3-diamine,
N'-(3-methoxy-8-methyl-7H-benzo[e]pyrido[4,3-b]indol-11-yl)-N,N-dimethyl-propane-1,3-diamine,
N'-(4-methoxy-8-methyl-7H-benzo[e]pyrido[4,3-b]indol-11-yl)-N,N-dimethyl-propane-1,3-diamine,
N-(3-amino-propyl)N'-[3-(3-methoxy-8-methyl-7H-benzo[e]pyrido[4,3-b]indol-11-ylamino)-propyl]butane-1,4-diamine,
N-(3-methoxy-8-methyl-7H-benzo[e]pyrido[4,3-b]indol-11-yl)-hexane-1,6-diamine,
N-[3-(3-methoxy-10-methyl-11H-benzo[g]pyrido[4,3-b]indol-7-ylamino)-propyl]-propane-1,3-diamine,
N-[3-(3-methoxy-10-methyl-11H-benzo[g]pyrido[4,3-b]indol-7-ylamino)-propyl]-N-methyl-propane-1,3-diamine,
N-[3-(3-methoxy-8-methyl-7H-benzo[e]pyrido[4,3-b]indol-11-ylamino)-propyl]-propane-1,3-diamine,
N-(5,6-dimethyl-5H-pyrido[3',4':4,5]pyrrolo[2,3-g]isoquinolin-10-yl)-N'-ethyl-propane-1,3-diamine,
6-methyl-5H-pyrido[3',4':4,5]pyrrolo[2,3-g]isoquinolin-10-yl-amine.

In a highly preferred embodiment, the pyrido-carbazole derivatives are selected from the group comprised of:
N'-(9-methoxy-5,6,11-trimethyl-6H-pyrido[4,3-b]carbazol-1-yl)-N,N-dimethyl-propane-1,3-diamine,
N'-(9-methoxy-6,11-dimethyl-5H-pyrido[4,3-b]carbazol-1-yl)-N,N-dimethyl-propane-1,3-diamine,
9-hydroxy-5-methyl-6H-pyrido[4,3-b]carbazol-1-yl acetic acid ester,
1-(3-dimethylamino-propylamino)5-methyl-6H-pyrido[4,3-b]carbazol-9-ol,
9-methoxy-5-methyl-6H-pyrido[4,3-b]carbazol-1-carbaldehyde oxime,
N'(9-methoxy-5-methyl-6H-pyrido[4,3-b]carbazol-11-yl)-N,N-dimethyl-propane-1,3-diamine,
N,N-diethyl-N'-(9-methoxy-5-methyl-6H-pyrido[4,3-b]carbazol-1-yl)-propane-1,3-diamine,
allyl-(9-methoxy-5,11-dimethyl-6H-pyrido[4,3-b]carbazol-1-yl)-amine,
N,N-diethyl-N4-(9-methoxy-5-methyl-6H-pyrido[4,3-b]carbazol-1-yl)-pentane-1,4-diamine,
9-methoxy-1-[6-(9-methoxy-5-methyl-6H-pyrido[4,3-b]carbazol-1-ylamino)-hexylamino]-2,5-dimethyl-6H-pyrido[4,3-b]carbazol-2-ium iodide,
{3-[4(3-amino-propyl)-piperazin-1-yl]-propyl}-9-methoxy-5-methyl-6H-pyrido[4,3-b]carbazol-1-yl)-amine,
(3-imidazol-1-yl-propyl)-9-methoxy-5-methyl-6H-pyrido[4,3-b]carbazol-1-yl)-amine,
(9-methoxy-5-methyl-6H-pyrido[4,3-b]carbazol-1-yl)-(2,2,6,6-tetramethyl-piperidin-4-yl)-amine,
N-ethyl-N-[3-(9-methoxy-5,11-dimethyl-6H-pyrido[4,3-b]carbazol-1-ylamino)-propyl]-succinamic acid,
5,11-dimethyl-1-(3-methyl-butylamino)-6H-pyrido[4,3-b]carbazol-9-ol, N'-(9-benzyloxy-6-methoxymethyl-5-methyl-6H-pyrido [4,3-b]carbazol-1-yl)-N,N-diethyl-propane-1,3-diamine,
1-(3-diethylamino-propylamino)-6-methoxymethyl-5-methyl-6H-pyrido[4,3-b]carbazol-9-ol,
9-methoxy-5-methyl-4,6-dihydro-3H-pyrido[453-b]carbazol,
1-(3-diethylamino-propylamino)-5,11-dimethyl-6H-pyrido[4,3-b]carbazol-9-ol,
N-(9-methoxy-5,11-dimethyl-6H-pyrido[4,3-b]carbazol-1-yl)-propane-1,3-diamine,
N,N-diethyl-N'-(9-methoxy-5,6,11-trimethyl-6H-pyrido [4,3-b]carbazol-1-yl)-ethane-1,2-diamine,
N-(9-methoxy-5-methyl-6H-pyrido[4,3-b]carbazol-1-yl)-propane-1,3-diamine,
9-methoxy-5-methyl-6H-pyrido[4,3-b]carbazol-1-carbonitrile,
1-(3-diethylamino-propylamino)-5-methyl-6H-pyrido[4,3-b]carbazol-9-ol,
(9-methoxy-5,11-dimethyl-6H-pyrido[4,3-b]carbazol-1-yl)-(3-morpholin-4-yl-propyl)-amine,
N-ethyl-N'-(9-methoxy-5-methyl-6H-pyrido[4,3-b]carbazol-1-yl)-propane-1,3-diamine,
N-(9-methoxy-5-methyl-6H-pyrido[4,3-b]carbazol-1-yl)-pentane-1,5-diamine
N-(9-methoxy-5-methyl-6H-pyrido[4,3-b]carbazol-1-yl)-hexane-1,6-diamine,
N'-(9-methoxy-5-methyl-6H-pyrido[4,3-b]carbazol-1-yl)-N,N-dimethyl-ethane-1,2-diamine,
N,N-diethyl-N'-(9-methoxy-5,11-dimethyl-6H-pyrido[4,3-b]carbazol-1-yl)-propane-1,3-diamine,
(9-methoxy-5-methyl-6H-pyrido[4,3-b]carbazol-1-yl)-(2-pyrrolidin-1-yl-ethyl)-amine,
3-(9-methoxy-5-methyl-6H-pyrido[4,3-b]carbazol-1-ylamino)-propane-1,2-diol,
1-diethylamino-3-(9-methoxy-5-methyl-6H-pyrido[4,3-b]carbazol-1-ylamino)-propan-2-ol,
decyl-(9-methoxy-5,11-dimethyl-6H-pyrido[4,3-b]carbazol-1-yl)-amine,
1-diethylamino-3-(9-methoxy-5,11-dimethyl-6H-pyrido [4,3-b]carbazol-1-ylamino)-propan-2-ol,
N,N-diethyl-N'-(9-methoxy-5,6-dimethyl-6H-pyrido[4,3-b]carbazol-1-yl)-ethane-1,2-diamine,
N-ethyl-N'-(9-methoxy-5,11-dimethyl-6H-pyrido[4,3-b] carbazol-1-yl)-propane-1,3-diamine,
N'-(7-methoxy-10,11-dimethyl-10H-pyrido[2,3-b]carbazol-4-yl)-N,N-dimethyl-propane-1,3-diamine,
N,N-diethyl-N'-(7-methoxy-10,11-dimethyl-10H-pyrido [2,3-b]carbazol-4-yl)-propane-1,3-diamine,
9-methoxy-5,11-dimethyl-6H-pyrido[4,3-b]carbazol-1-yl-amine,
N,N-diethyl-N'-(7-methoxy-11-methyl-10H-pyrido[2,3-b]carbazol-4-yl)-propane-1,3-diamine,
N,N-diethyl-N'-(7-methoxy-5,11-dimethyl-10H-pyrido [2,3-b]carbazol-4yl)-propane-1,3-diamine.

In another highly preferred embodiment, the pyrido-pyrrolo-isoquinoline derivatives are selected from the group comprised of:
10-chloro-2,6-dimethyl-2H-pyrido[3',4':4,5]pyrrolo[2,3-g]isoquinoline,
N'-(6,11-dimethyl-5H-pyrido[3',4':4,5]pyrrolo[2,3-g]isoquinolin-10-yl)-N,N-dimethyl-propane-1,3-diamine,
N,N-dimethyl-N'-(6-methyl-5H-pyrido[3',4':4,5]pyrrolo [2,3-g]isoquinolin-10-yl)-propane-1,3-diamine,
N-ethyl-N-[3-(6-methyl-5H-pyrido[3',4':4,5]pyrrolo[2,3-g]isoquinolin-10-ylamino)-propyl]-succinamic acid,
2-{(2-hydroxy-ethyl)-[3-(6-methyl-5H-pyrido[3',4':4,5] pyrrolo[2,3-g]isoquinolin-10-ylamino}propyl]-amino-ethanol,
N,N-diethyl-N'-(6-methyl-5H-pyrido[3',4':4,5]pyrrolo[2,3-g]isoquinolin-10-yl)-ethane-1,2-diamine,
N-(6-methyl-5H-pyrido[3',4':4,5]pyrrolo[2,3-g]isoquinolin-10-yl)-propane-1,3-diamine,
N-3-(5,6-dimethyl-5H-pyrido[3',4':4,5]pyrrolo[2,3-g]isoquinolin-10-yl)-N,N-1-diethyl-butane-1,3-diamine,
N-(6,11-dimethyl-5H-pyrido[3',4':4,5]pyrrolo[2,3-g]isoquinolin-10-yl)-N'-ethyl-propane-1,3-diamine,
N'-(5)6-dimethyl-5H-pyrido[3',4':4,5]pyrrolo[2,3-g]isoquinolin-10-yl)-N,N-dimethyl-propane-1,3-diamine,
N-(5,6-dimethyl-5H-pyrido[3',4':4,5]pyrrolo[2,3-g]isoquinolin-10-yl)-N'-ethyl-propane-1,3-diamine,
(3-imidazol-1-yl-propyl)-(6-methyl-5H-pyrido[3',4':4,5] pyrrolo[2,3-g]isoquinolin-10-yl)-amine,
N-N-diethyl-N'-(6-methyl-5H-pyrido[3',4':4,5]pyrrolo[2,3-g]isoquinolin-10-yl)-propane-1,3-diamine,
N-1,N-10-Bis-(3-diethylamino-propyl)-3,6-dimethyl-5H-pyrido[3',4':4,5]pyrrolo[2,3-g]isoquinoline-1,10-diamine,
N,N-dimethyl-N'-(10,11-dimethyl-10H-pyrido[3'4':4,5] pyrrolo[3,2-g]quinoline)4-yl-propane-1,3-diamine,
N,N-diethyl-N'-(10,11-dimethyl-10H-pyrido[3',4':4,5] pyrrolo[3,2-g]quinoline)-4-yl-propane-1,3-diamine,
N,N-diethyl-N'-(11-methyl-10H-pyrido[3',4':4,5]pyrrolo [3,2-g]quinoline)-4-yl-propane-1,3-diamine,
N,N-dimethyl-N'-(11-methyl-10H-pyrido[3',4':4,5]pyrrolo[3,2-g]quinoline)-4-yl-propane-1,3-diamine,
N-(5,6-dimethyl-5H-pyrido[3',4':4,5]pyrrolo[2,3-g]isoquinolin-10-yl)-N'-ethyl-propane-1,3-diamine,
6-methyl-5H-pyrido[3',4':4,5]pyrrolo[2,3-g]isoquinolin-10-yl-amine.

In another highly preferred embodiment, the benzo-pyrido-indole derivatives are selected from the group comprised of:
N-(3-methoxy-10-methyl-11H-benzo[g]pyrido[4,3-b]indol-7-yl)-butane-1,4-diamine,
8-methyl-11-(3-methylamino-propylamino)-7H-benzo[e] pyrido[4,3-b]indol-3-ol,
N-(5,6-dimethyl-5H-benzo[f]pyrido[4,3]indol-1-yl)-N'-ethyl-propane-1,3-diamine,
N'-(9-methoxy-5,6-dimethyl-5H-benzo[f]pyrido[4,3-b] indol-1-yl)-N,N-dimethyl-propane-1,3-diamine,
1-(3-dimethylamino-propylamino)-5,6-dimethyl-5H-benzo[f]pyrido[4,3-b]indol-9-ol,
N-(3-methoxy-8-methyl-7H-benzo[e]pyrido[4,3-b]indol-11-yl)-N'-methyl-propane-1,3-diamine,
5-(7-chloro-10-methyl-11H-benzo[g]pyrido[4,3-b]indol-3-yloxy)-pentanoic acid ethyl ester,
11-(3-dimethylamino-propylamino)-8-ethyl-7H-benzo[e] pyrido[4,3-b]indol-3-ol,
7-(3-diethylamino-propylamino)10,11-dimethyl-11H-benzo[g]pyrido[4,3-b]indol-4-ol,
11-(3-dimethylamino-propylamine)-7H-benzo[e]pyrido [4,3-b]indol-3-ol,
N'-(3-methoxy-7H-benzo[e]pyrido[4,3-b]indol-11-yl)-N, N-dimethyl-propane-1,3-diamine,
N'-8-ethyl-3-methoxy-7-methyl-7H-benzo[e]pyrido[4,3-b]indol-11-yl)-N,N-dimethyl-propane-1,3-diamine,
11-(3-dimethylamino-propylamino)-8-methyl-7H-benzo [e]pyrido[4,3-b]indol-2-ol,
N,N-diethyl-N'-(3-methoxy-10,11-dimethyl-11H-benzo [g]pyrido[4,3-b]indol-7-yl)-propane-1,3-diamine,
11-(3-dimethylamino-propylamino)-7,8-dimethyl-7H-benzo[e]pyrido[4,3-b]indol-3-ol, 7-(3-dimethylamino-propylamino)-10-methyl-11H-benzo[g]pyrido[4,3-b]indol-4-ol,
N'-(2-methoxy-8-methyl-7H-benzo[e]pyrido[4,3-b]indol-11-yl)-N,N-dimethyl-propane-1,3-diamine,
N'-(10,11-dimethyl-11H-benzo[g]pyrido[4,3-b]indol-7-yl)-N,N-diethyl-propane-1,3-diamine,
N'-(7,8-dimethyl-7H-benzo[e]pyrido[4,3-b]indol-11-yl)-N,N-dimethyl-propane-1,3-diamine,
N,N-dimethyl-N'-(10-methyl-11H-benzo[g]pyrido[4,3-b]indol-7-yl)-propane-1,3-diamine,
7-(3-diethylamino-propylamino)-10,11-dimethyl-11H-benzo[g]pyrido[4,3-b]indol-3-ol,
N,N-diethyl-N'-(10-methyl-11H-benzo[g]pyrido[4,3-b]indol-7-yl)-propane-1,3-diamine,
4-methoxy-10-methyl-11H-benzo[g]pyrido[4,3-b]indol-7-ylamine,
N,N-diethyl-N'-(3-methoxy-10-methyl-11H-benzo[g]pyrido[4,3-b]indol-7-yl)-propane-1,3-diamine,
N'-(4-methoxy-10,11-dimethyl-11H-benzo[g]pyrido[4,3-b]indol-7-yl)-N,N-dimethyl-propane-1,3-diamine,
7-(3-(dimethylamino-propylamino)-10,11-dimethyl-11H-benzo[g]pyrido[4,3-b]indol-4-ol,
N,N-dimethyl-N'-(8-methyl-7H-benzo[e]pyrido[4,3-b]indol-11-yl)-propane-1,3-diamine,
11-(3-dimethylamino-2-methyl-propylammo)-8-methyl-7H-benzo[e]pyrido[4,3-b]indol-3-ol,
N-(3-methoxy-8-methyl-7H-benzo[e]pyrido[4,3-b]indol-11-yl)-propane-1,3-diamine,
11-(3-amino-propylamino)-8-methyl-7H-benzo[e]pyrido[4,3-b]indol-3-ol,
N-(3-methoxy-10-methyl-11H-benzo[g]pyrido[4,3-b]indol-7-yl)-propane-1,3-diamine,
N'-(3-methoxy-8-methyl-7H-benzo[e]pyrido [4,3-b]indol-11-yl)-N,N-dimethyl-propane-1,3-diamine,
N'-(4-methoxy-8-methyl-7H-benzo [e]pyrido[4,3-b]indol-11-yl)-N,N-dimethyl-propane-1,3-diamine,
N-(3-amino-propyl)N'-[3-(3-methoxy-8-methyl-7H-benzo[e]pyrido[4,3-b]indol-11-ylamino)-propyl]butane-1,4-diamine,
N-(3-methoxy-8-methyl-7H-benzo[e]pyrido[4,3-b]indol-11-yl)-hexane-1,6-diamine,
N-[3-(3-methoxy-10-methyl-11H-benzo[g]pyrido[4,3-b]indol-7-ylamino)-propyl]-propane-1,3-diamine,
N-[3-(3-methoxy-10-methyl-11H-benzo[g]pyrido[4,3-b]indol-7-ylamino)-propyl]-N-methyl-propane-1,3-diamine,
N-[3-(3-methoxy-8-methyl-7H-benzo[e]pyrido[4,3-b]indol-11-ylamino)-propyl]-propane-1,3-diamine.

In an embodiment even more preferred, the indole derivatives are selected from the group comprised of:
N'-(9-methoxy-5,6,11-trimethyl-6H-pyrido[4,3-b]carbazol-1-yl)-N,N-dimethyl-propane-1,3-diamine,
N'-(9-methoxy-6,11-dimethyl-6H-pyrido[4,3-b]carbazol-1-yl)-N,N-dimethyl-propane-1,3-diamine,
10-chloro-2,6-dimethyl-2H-pyrido[3',4':4,5]pyrrolo[2,3-g]isoquinoline,
1-(3-dimethylamino-propylamino)5-methyl-6H-pyrido[4,3-b]carbazol-9-ol,
N'(9-methoxy-5-methyl-6H-pyrido[4,3-b]carbazol-11-yl)-N,N-dimethyl-propane-1,3-diamine,
allyl-(9-methoxy-5,11-dimethyl-6H-pyrido[4,3-b]carbazol-1-yl)-amine,
N,N-diethyl-N4-(9-methoxy-5-methyl-6H-pyrido[4,3-b]carbazol-1-yl)-pentane-1,4-diamine,
9-methoxy-1-[6-(9-methoxy-5-methyl-6H-pyrido[4,3-b]carbazol-1-ylamino)-hexylamino]-2,5-dimethyl-6H-pyrido[4,3-b]carbazol-2-ium iodide,
(3-imidazol-1-yl-propyl)-9-methoxy-5-methyl-6H-pyrido[4,3-b]carbazol-1-yl)-amine,
(9-methoxy-5-methyl-6H-pyrido[4,3-b]carbazol-1-yl)-(2,2,6,6-tetramethyl-piperidin-4-yl)-amine,
N-ethyl-N-[3-(9-methoxy-5,11-dimethyl-6H-pyrido[4,3-b]carbazol-1-ylamino)-propyl]-succinamic acid,
N-ethyl-N-[3-(6-methyl-5H-pyrido[3',4':4,5]pyrrolo[2,3-g]isoquinolin-10-ylamino)-propyl]-succinamic acid,
5,11-dimethyl-1-(3-methyl-butylamino)-6H-pyrido[4,3-b]carbazol-9-ol,
N,N-diethyl-N'-(6-methyl-5H-pyrido[3',4':4,5]pyrrolo[2,3-g]isoquinolin-10-yl)-ethane-1,2-diamine,
1-(3-diethylamino-propylamino)-5,11-dimethyl-6H-pyrido[4,3-b]carbazol-9-ol,
N,N-diethyl-N'-(9-methoxy-5,6,11-trimethyl-6H-pyrido[4,3-b]carbazol-1-yl)-ethane-1,2-diamine,
N'-(5,6-dimethyl-5H-pyrido[3',4':4,5]pyrrolo[2,3-g]isoquinolin-10-yl)-N,N-dimethyl-propane-1,3-diamine,
1-(3-diethylamino-propylamino)-5-methyl-6H-pyrido[4,3-b]carbazol-9-ol,
N,N-diethyl-N'-(9-methoxy-5,11-dimethyl-6H-pyrido[4,3-b]carbazol-1-yl)-propane-1,3-diamine,
1-diethylamino-3-(9-methoxy-5-methyl-6H-pyrido[4,3-b]carbazol-1-ylamino)-propan-2-ol,
N-(3-methoxy-10-methyl-11H-benzo[g]pyrido[4,3-b]indol-7-yl)-butane-1,4-diamine,
N,N-diethyl-N'-(9-methoxy-5,6-dimethyl-6H-pyrido[4,3-b]carbazol-1-yl)-ethane-1,2-diamine,
N,N-diethyl-N'-(6-methyl-5H-pyrido[3',4':4,5]pyrrolo[2,3-g]isoquinoline-10-yl)-propane-1,3-diamine,
N-(3-methoxy-8-methyl-7H-benzo[e]pyrido[4,3-b]indol-11-yl)-N'-methyl-propane-1,3-diamine,
4-methoxy-10-methyl-11H-benzo[g]pyrido[4,3-b]indol-7-ylamine,
N-(3-methoxy-10-methyl-11H-benzo[g]pyrido[4,3-b]indol-7-yl)-propane-1,3-diamine,
N'-(3-methoxy-8-methyl-7H-benzo[e]pyrido[4,3-b]indol-11-yl)-N,N-dimethyl-propane-1,3-diamine,
N-[3-(3-methoxy-10-methyl-11H-benzo[g]pyrido[4,3-b]indol-7-ylamino)-propyl]-N-methyl-propane-1,3-diamine,
6-methyl-5H-pyrido[3',4':4,5]pyrrolo[2,3-g]isoquinolin-10-yl-amine.

The present invention also relates to the following compounds:
10-chloro-2,6-dimethyl-2H-pyrido[3',4':4,5]pyrrolo[2,3-g]isoquinoline,
(9-methoxy-6-methyl-6H-pyrido[4,3-b]carbazol-1-yl)-(2,2,6,6-tetramethyl-piperidin-4-yl)-amine,
N-ethyl-N-[3-(9-methoxy-5,11-dimethyl-6H-pyrido[4,3-b]carbazol-1-ylamino)-propyl]-succinamic acid,
N-ethyl-N-[3-(6-methyl-5H-pyrido[3',4':4,5]pyrrolo[2,3-g]isoquinolin-10-ylamino)-propyl]-succinamic acid,
9-methoxy-5-methyl-4,6-dihydro-3H-pyrido[4,3-b]carbazole,
N-(3-amino-propyl)N'-[3-(3-methoxy-8-methyl-7H-benzo[e]pyrido[4,3-b]indol-11-ylamino)-propyl]butane-1,4-diamine,
N-(3-methoxy-8-methyl-7H-benzo[e]pyrido[4,3-b]indol-11-yl)-hexane-1,6-diamine,
N-[3-(3-methoxy-10-methyl-11H-benzo[g]pyrido[4,3-b]indol-7-ylamino)-propyl]-propane-1,3-diamine,
N-[3-(3-methoxy-8-methyl-7H-benzo[e]pyrido[4,3-b]indol-11-ylamino)-propyl]-propane-1,3-diamine.

Another object of the invention is the compounds such as previously described for use as medicines.

In a preferred embodiment, the compounds according to the invention have the capacity to inhibit pre-messenger RNA splicing processes that are either constitutive, or, more specifically., dependent on regulatory sequences termed ESEs (exonic splicing enhancers), ISEs (intronic splicing enhancers), ESSs (exonic splicing silencers) and ISSs (intronic splicing silencers).

In a still more preferred embodiment, the splicing processes are either constitutive and/or dependent on ESE regulatory sequences.

In another preferred embodiment according to the invention, the diseases related to the splicing process are the genetic diseases resulting from splicing-process modification such as for example Frasier syndrome, frontotemporal dementia related to chromosome 17 (a form of Parkinson's), Leigh syndrome (a type of encephalopathy), atypical cystic fibrosis, certain neuropathologies, such as in particular Alzheimer's, related to Tau protein mutation, amyotrophy that influences the SMN (survival motor neuron) gene, depression related to disturbances in serotonin splicing and certain cancers in which the overall splicing process is affected (notably breast cancer, colon cancer and certain lymphomas).

In another preferred embodiment, the diseases related to the splicing process are diseases of viral origin for which ESE sequences are identified.

Preferentially, the viral disease is AIDS.

In an embodiment according to the invention, the aforementioned medicine also includes an excipient that makes it possible to formulate the compounds according to formula I and the aforementioned medicine is presented in solid or liquid form to be prepared and to be administered by intravenous route.

The compounds according to the invention will be administered preferably by intravenous route at a concentration of 80-100 mg/m$^2$ (cf. Paoletti C. et al., Antitumor activity, pharmacology, and toxicity of ellipticine, ellipticinium, and 9-hydroxy derivatives: preliminary clinical trials of 2-methyl-9-hydroxy ellipticinium (NSC 264-137) in Recent Results in Cancer Research, vol 74, pp. 108-123, 1980, G. Mathé and F. M. Muggia, Eds (Springer-Verlag Pbl). The concentration will be chosen by those skilled in the art according to the organ or tissue to be treated, the state of advancement of the disease and the targeting method used.

EXAMPLE 1

In Vitro Inhibition of Splicing of Two Types of Model pre-mRNAs

The compounds presented in Tables 1 and 2 below were tested in a concentration range of 1 µM, 10 µM and 100 µM, and were selected initially on the basis of their capacity to inhibit, in vitro, the splicing of two types of model pre-mRNAs.

TABLE 1

| Molecule code | Chemical formula | Nomenclature |
| --- | --- | --- |
| C1 | | N'-(9-methoxy-5,6,11-trimetyl-6H-pyrido[4,3-b]carbazol-1-yl)-N,N-dimethyl-propane-1,3-diamine |
| C2 | | N'-(9-methoxy-6,11-dimethyl-6H-pyrido[4,3-b]carbazol-1-yl)-N,N-dimethyl-propane-1,3-diamine |
| C3 | | 10-chloro-2,6-dimethyl-2H-pyrido[3',4':4,5]pyrrolo[2,3-g]isoquinoline |

TABLE 1-continued

| Molecule code | Chemical formula | Nomenclature |
| --- | --- | --- |
| C4 | | 9-hydroxy-5-methyl-6H-pyrido[4,3-b]carbazol-1-yl acetic acid ester |
| C5 | | 1-(3-dimethylamino-propylamino)5-methyl-6H-pyrido[4,3-b]carbazol-9-ol |
| C6 | | 9-methoxy-5-methyl-6H-pyrido[4,3-b]carbazol-1-carbaldehyde oxime |
| C7 | | N'(9-methoxy-5-methyl-6H-pyrido[4,3-b]carbazol-11-yl)-N,N-dimethyl-propane-1,3-diamine |
| C8 | | N,N-diethyl-N'-(9-methoxy-5-methyl-6H-pyrido[4,3-b]carbazol-1-yl)-propane-1,3-diamine |
| C9 | | N'-(6,11-dimethyl-5H-pyrido[3',4':4,5]pyrrolo[2,3-g]isoquinolin-10-yl)-N,N-dimethyl-propane-1,3-diamine |

TABLE 1-continued

| Molecule code | Chemical formula | Nomenclature |
| --- | --- | --- |
| C10 | 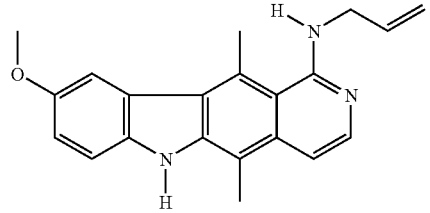 | allyl-(9-methoxy-5,11-dimethyl-6H-pyrido[4,3-b]carbazol-1-yl)-amine |
| C11 | 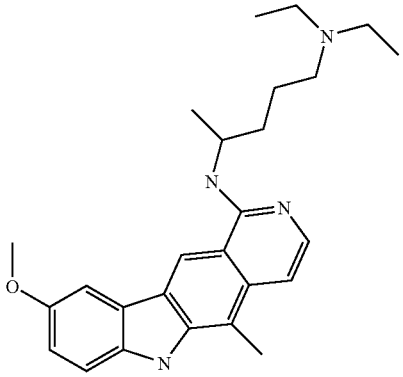 | N,N-diethyl-N4-(9-methoxy-5-methyl-6H-pyrido[4,3-b]carbazol-1-yl)-pentane-1,4-diamine |
| C12 | 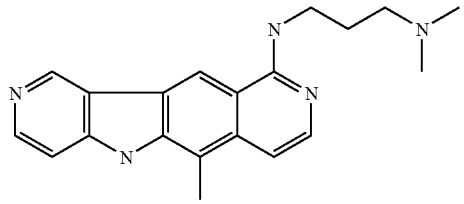 | N,N-dimethyl-N'-(6-methyl-5H-pyrido[3',4':4,5]pyrrolo[2,3-g]isoquinolin-10-yl)-propane-1,3-diamine |
| C13 | 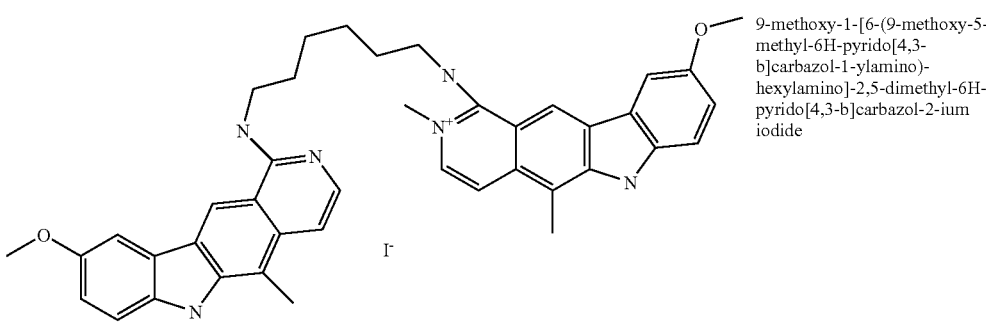 | 9-methoxy-1-[6-(9-methoxy-5-methyl-6H-pyrido[4,3-b]carbazol-1-ylamino)-hexylamino]-2,5-dimethyl-6H-pyrido[4,3-b]carbazol-2-ium iodide |
| C14 | 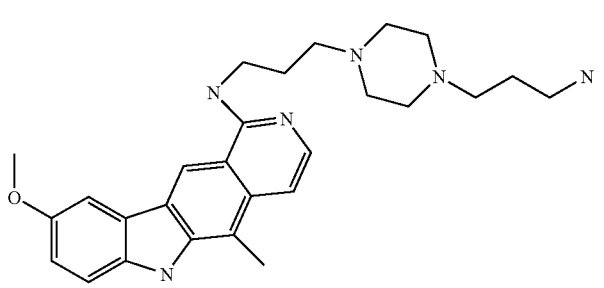 | {3-[4(3-amino-propyl)-piperazin-1-yl]-propyl}-9-methoxy-5-methyl-6H-pyrido[4, 3-b]carbazol-1-yl)-amine |

US 7,989,467 B2

21　　　　　　　　　　　　　　　　　22

TABLE 1-continued

| Molecule code | Chemical formula | Nomenclature |
|---|---|---|
| C15 | 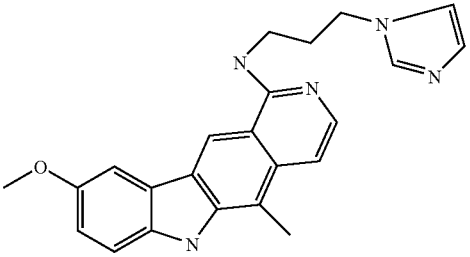 | (3-imidazol-1-yl-propyl)-9-methoxy-5-methyl-6H-pyrido[4,3-b]carbazol-1-yl)-amine |
| C16 | 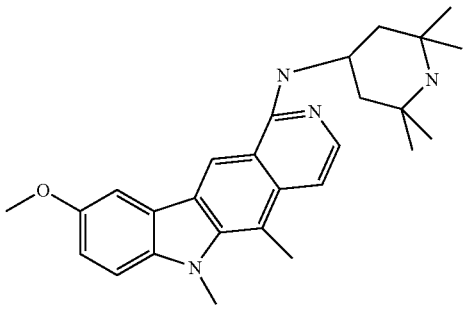 | (9-methoxy-5-methyl-6H-pyrido[4,3-b]carbazol-1-yl)-(2,2,6,6-tetramethyl-piperidin-4-yl)-amine |
| C17 | 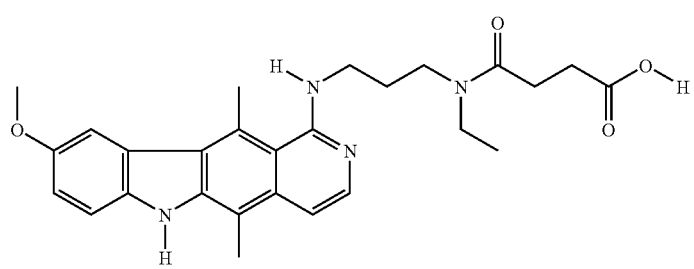 | N-ethyl-N-[3-(9-methoxy-5,11-dimethyl-6H-pyrido[4,3-b]carbazol-1-ylamino)-propyl]-succinamic acid |
| C18 | 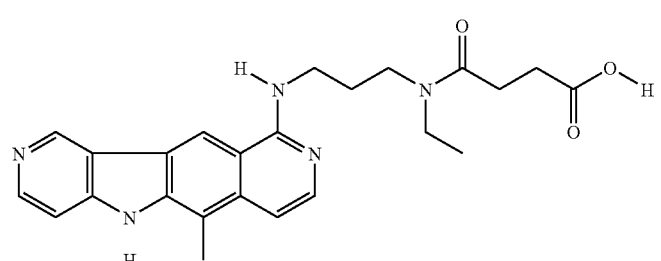 | N-ethyl-N-[3-(6-methyl-5H-pyrido[3',4':4,5]pyrrolo[2,3-g]isoquinolin-10-ylamino)-propyl]-succinamic acid |
| C19 | 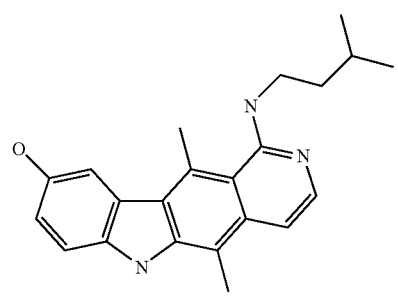 | 5,11-dimethyl-1-(3-methyl-butylamino)-6H-pyrido[4,3-b]carbazol-9-ol |

TABLE 1-continued

| Molecule code | Chemical formula | Nomenclature |
|---|---|---|
| C20 | 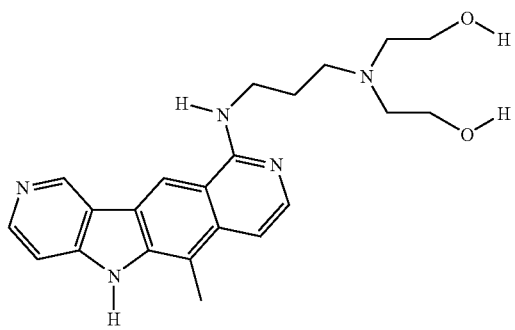 | 2-{(2-hydroxy-ethyl)-[3-(6-methyl-5H-pyrido[3,4':4,5]pyrrolo[2,3-g]isoquinolin-10-ylamino}propyl]-amino-ethanol |
| C21 | 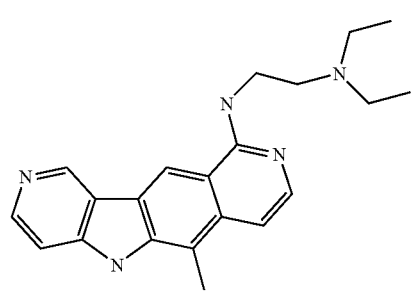 | N,N-diethyl-N'-(6-methyl-5H-pyrido[3',4':4,5]pyrrolo[2,3-g]isoquinolin-10-yl)-ethane-1,2-diamine |
| C22 | 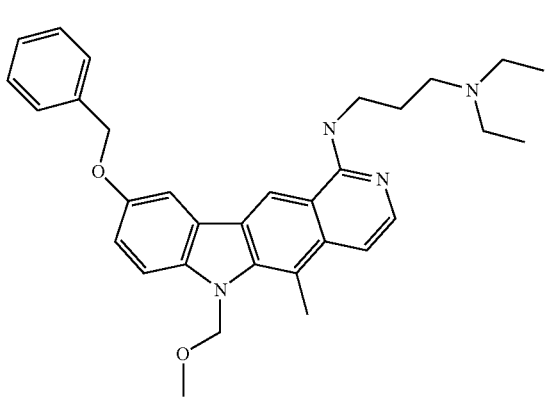 | N'-(9-benzyloxy-6-methoxymethyl-5-methyl-6H-pyrido[4,3-b]carbazol-1-yl)-N,N-diethyl-propane-1,3-diamine |
| C23 | 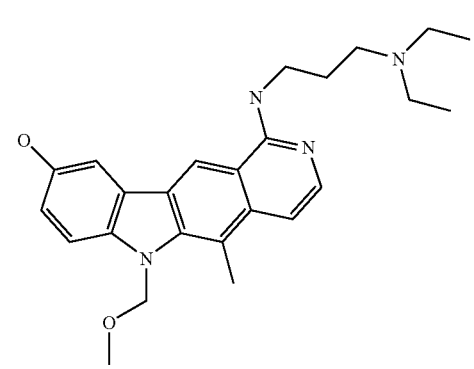 | 1-(3-diethylamino-propylamino)-6-methoxymethyl-5-methyl-6H-pyrido[4,3-b]carbazol-9-ol |
| C24 | 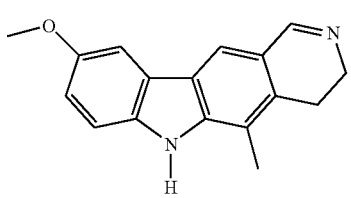 | 9-methoxy-5-methyl-4,6-dihydro-3H-pyrido[4,3-b]carbazol |

TABLE 1-continued

| Molecule code | Chemical formula | Nomenclature |
|---|---|---|
| C25 | | N-(6-methyl-5H-pyrido[3',4':4,5]pyrrolo[2,3-g]isoquinolin-10-yl)-propane-1,3-diamine |
| C26 | | 1-(3-diethylamino-propylamino)-5,11-dimethyl-6H-pyrido[4,3-b]carbazol-9-ol |
| C27 | | N-(9-methoxy-5,11-dimethyl-6H-pyrido[4,3-b]carbazol-1-yl)-propane-1,3-diamine |
| C28 | | N-3-(5,6-dimethyl-5H-pyrido[3',4':4,5]pyrrolo[2,3-g]isoquinolin-10-yl)-N,N-1-diethyl-butane-1,3-diamine |
| C29 | | N,N-diethyl-N'-(9-methoxy-5,6,11-trimethyl-6H-pyrido[4,3-b]carbazol-1-yl)-ethane-1,2-diamine |
| C30 | | N-(6,11-dimethyl-5H-pyrido[3',4':4,5]pyrrolo[2,3-g]isoquinolin-10-yl)-N'-ethyl-propane-1,3-diamine |

TABLE 1-continued

| Molecule code | Chemical formula | Nomenclature |
| --- | --- | --- |
| C31 | | N-(9-methoxy-5-methyl-6H-pyrido[4,3-b]carbazol-1-yl)-propane-1,3-diamine |
| C32 | | N'-(5,6-dimethyl-5H-pyrido[3'4':4,5]pyrrolo[2,3-g]isoquinolin-10-yl)-N,N-dimethyl-propane-1,3-diamine |
| C33 | | N-(5,6-dimethyl-5H-pyrido[3'4':4,5]pyrrolo[2,3-g]isoquinolin-10-yl)-N'-ethyl-propane-1,3-diamine |
| C34 | | 9-methoxy-5-methyl-6H-pyrido[4,3-b]carbazol-1-carbonitrile |
| C35 | | 1-(3-diethylamino-propylamino)-5-methyl-6H-pyrido[4,3-b]carbazol-9-ol |
| C36 | | (9-methoxy-5,11-dimethyl-6H-pyrido[4,3-b]carbazol-1-yl)-(3-morpholin-4-yl-propyl)-amine |

TABLE 1-continued

| Molecule code | Chemical formula | Nomenclature |
|---|---|---|
| C37 | | N-ethyl-N'-(9-methoxy-5-methyl-6H-pyrido[4,3-b]carbazol-1-yl)-propane-1,3-diamine |
| C38 | | N-(9-methoxy-5-methyl-6H-pyrido[4,3-b]carbazol-1-yl)-pentane-1,5-diamine |
| C39 | | N-(9-methoxy-5-methyl-6H-pyrido[4,3-b]carbazol-1-yl)-hexane-1,6-diamine |
| C40 | | N'-(9-methoxy-5-methyl-6H-pyrido[4,3-b]carbazol-1-yl)-N,N-dimethyl-ethane-1,2-diamine |
| C41 | | N,N-diethyl-N'-(9-methoxy-5,11-dimethyl-6H-pyrido[4,3-b]carbazol-1-yl)-propane-1,3-diamine |

TABLE 1-continued

| Molecule code | Chemical formula | Nomenclature |
|---|---|---|
| C42 | 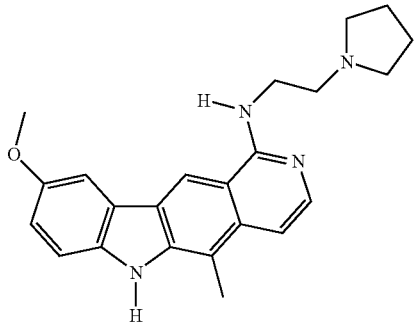 | (9-methoxy-5-methyl-6H-pyrido[4,3-b]carbazol-1-yl)-(2-pyrrolidin-1-yl-ethyl)-amine |
| C43 | 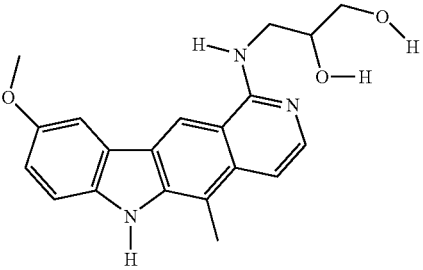 | 3-(9-methoxy-5-methyl-6H-pyrido[4,3-b]carbazol-1-ylamino)-propane-1,2-diol |
| C44 | 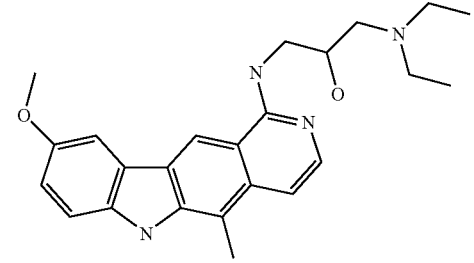 | 1-diethylamino-3-(9-methoxy-5-methyl-6H-pyrido[4,3-b]carbazol-1-ylamino)-propan-2-ol |
| C45 | 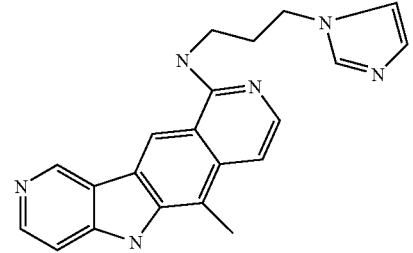 | (3-imidazol-1-yl-propyl)-(6-methyl-5H-pyrido[3',4':4,5]pyrrolo[2,3-g]isoquinolin-10-yl)-amine |
| C46 | 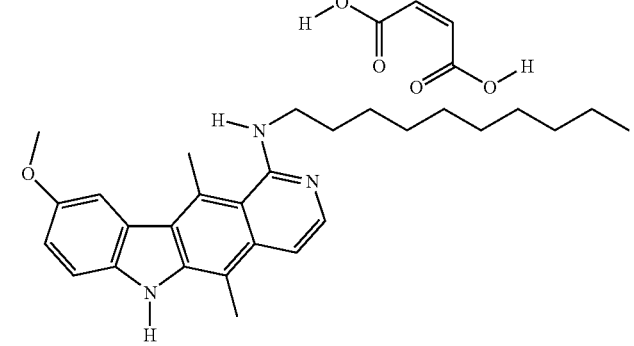 | decyl-(9-methoxy-5,11-dimethyl-6H-pyrido[4,3-b]carbazol-1-yl)-amine |

TABLE 1-continued

| Molecule code | Chemical formula | Nomenclature |
|---|---|---|
| C47 | 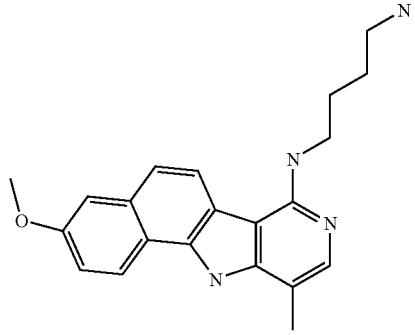 | N-(3-methoxy-10-methyl-11H-benzo[g]pyrido[4,3-b]indol-7-yl)-butane-1,4-diamine |
| C48 | 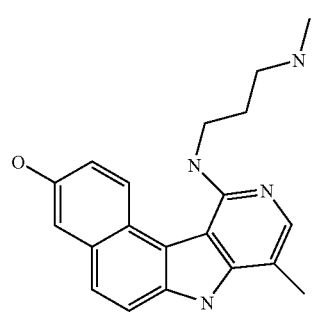 | 8-methyl-11-(3-methylamino-propylamino)-7H-benzo[e]pyrido[4,3-b]indol-3-ol |
| C49 | 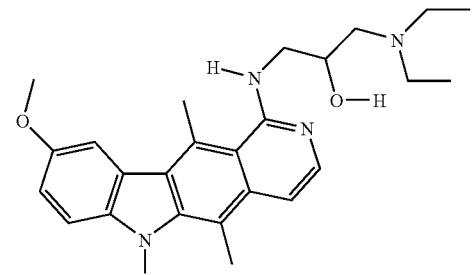 | 1-diethylamino-3-(9-methoxy-5,11-dimethyl-6H-pyrido[4,3-b]carbazol-1-ylamino)-propan-2-ol |
| C50 | 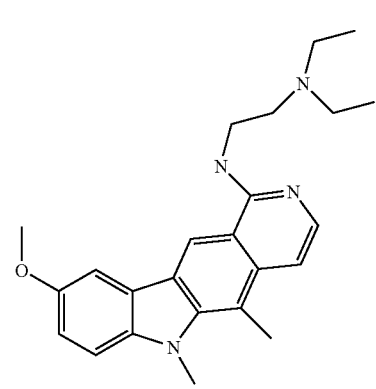 | N,N-diethyl-N'-(9-methoxy-5,6-dimethyl-6H-pyrido[4,3-b]carbazol-1-yl)-ethane-1,2-diamine |
| C51 | 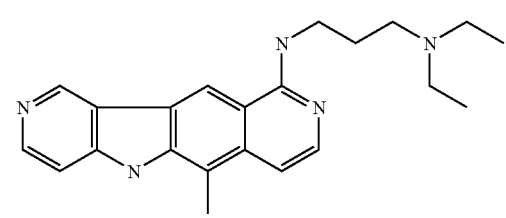 | N-N,diethyl-N'-(6-methyl-5H-pyrido[3',4':4,5]pyrrolo[2,3-g]isoquinolin-10-yl)-propane-1,3-diamine |

TABLE 1-continued

| Molecule code | Chemical formula | Nomenclature |
|---|---|---|
| C52 | | N-1,N-10-Bis-(3-diethylamino-propyl)-3,6-dimethyl-5H-pyrido[3',4':4,5]pyrrolo[2,3-g]isoquinoline-1,10-diamine |
| C53 | | N-ethyl-N'-(9-methoxy-5,11-dimethyl-6H-pyrido[4,3-b]carbazol-1-yl)-propane-1,3-diamine |
| C54 | | N-(5,6-dimethyl-5H-benzo[f]pyrido∝3]indol-1-yl)-N'-ethyl-propane-1,3-diamine |
| C55 | | N'-(9-methoxy-5,6-dimethyl-5H-benzo[f]pyrido[4,3-b]indol-1-yl)-N,N-dimethyl-propane-1,3-diamine |
| C56 | | 1-(3-dimethylamino-propylamino)-5,6-dimethyl-5H-benzo[f]pyrido[4,3-b]indol-9-ol |

TABLE 1-continued

| Molecule code | Chemical formula | Nomenclature |
|---|---|---|
| C57 | | N-(3-methoxy-8-methyl-7H-benzo[e]pyrido[4,3-b]indol-11-yl)-N'-methyl-propane-1,3-diamine |
| C58 | | 5-(7-chloro-10-methyl-11H-benzo[g]pyrido[4,3-b]indol-3-yloxy)-pentanoic acid ethyl ester |
| C59 | | N,N-dimethyl-N'-(10,11-dimethyl-10H-pyrido[3'4':4,5]pyrrolo[3,2-g]quinoline)4-yl-propane-1,3-diamine |
| C60 | | N,N-diethyl-N'-(10,11-dimethyl-10H-pyrido[3'4':4,5]pyrrolo[3,2-g]quinoline)-4-yl-propane-1,3-diamine |
| C61 | | N'-(7-methoxy-10,11-dimethyl-10H-pyrido[2,3-b]carbazol-4-yl)-N,N-dimethyl-propane-1,3-diamine |
| C62 | | N,N-diethyl-N'-(7-methoxy-10,11-dimethyl-10H-pyrido[2,3-b]carbazol-4-yl)-propane-1,3-diamine |

TABLE 1-continued

| Molecule code | Chemical formula | Nomenclature |
|---|---|---|
| C63 | 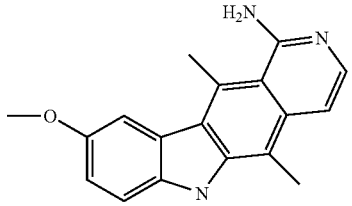 | 9-methoxy-5,11-dimethyl-6H-pyrido[4,3-b]carbazol-1-yl-amine |
| C64 | 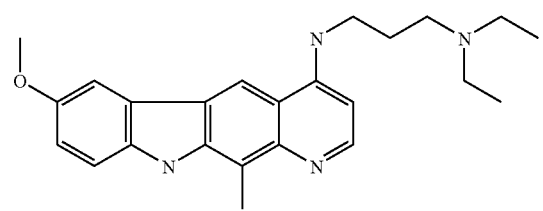 | N,N-diethyl-N'-(7-methoxy-11-methyl-10H-pyrido[2,3-b]carbazol-4-yl)-propane-1,3-diamine |
| C65 | 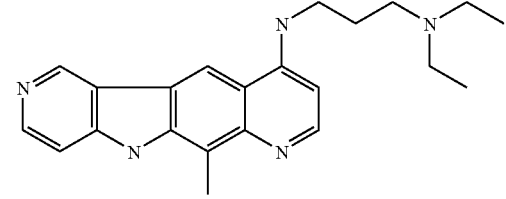 | N,N-diethyl-N'-(11-methyl-10H-pyrido[3',4':4,5]pyrrolo[3,2-g]quinoline)-4-yl-propane-1,3-diamine |
| C66 | 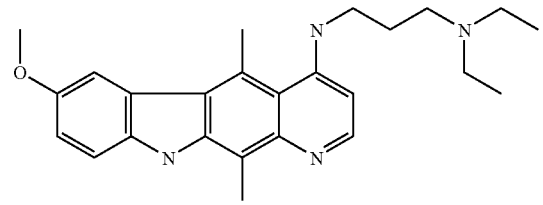 | N,N-diethyl-N'-(7-methoxy-5,11-dimethyl-10H-pyrido[2,3-b]carbazol-4yl)-propane-1,3-diamine |
| C67 | 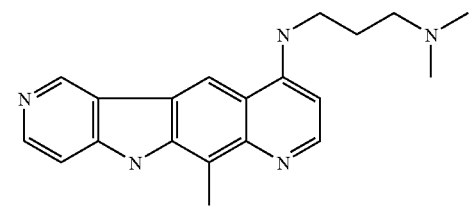 | N,N-dimethyl-N'-(11-methyl-10H-pyrido[3',4':4,5]pyrrolo[3,2-g]quinoline)-4-yl-propane-1,3-diamine |
| C68 | 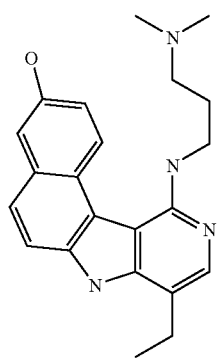 | 11-(3-dimethylamino-propylamino)-8-ethyl-7H-benzo[e]pyrido[4,3-b]indol-3-ol |

TABLE 1-continued

| Molecule code | Chemical formula | Nomenclature |
|---|---|---|
| C69 | | 7-(3-diethylamino-propylamino)10,11-dimethyl-11H-benzo[g]pyrido[4,3-b]indol-4-ol |
| C70 | | 11-(3-dimethylamino-propylamine)-7H-benzo[e]pyrido[4,3-b]indol-3-ol |
| C71 | | N'-(3-methoxy-7H-benzo[e]pyrido[4,3-b]indol-11-yl)-N,N-dimethyl-propane-1,3-diamine |
| C72 | | N'-8-ethyl-3-methoxy-7-methyl-7H-benzo[e]pyrido[4,3-b]indol-11-yl)-N,N-dimethyl-propane-1,3-diamine |
| C73 | | 11-(3-dimethylamino-propylamino)-8-methyl-7H-benzo[e]pyrido[4,3-b]indol-2-ol |

TABLE 1-continued

| Molecule code | Chemical formula | Nomenclature |
|---|---|---|
| C74 | | N,N-diethyl-N'-(3-methoxy-10,11-dimethyl-11H-benzo[g]pyrido[4,3-b]indol-7-yl)-propane-1,3-diamine |
| C75 | | 11-(3-dimethylamino-propylamino)-7,8-dimethyl-7H-benzo[e]pyrido[4, 3-b]indol-3-ol |
| C76 | | 7-(3-dimethylamino-propylamino)-10-methyl-11H-benzo[g]pyrido[4,3-b]indol-4-ol |
| C77 | | N'-(2-methoxy-8-methyl-7H-benzo[e]pyrido[4,3-b]indol-11-yl)-N,N-dimethyl-propane-1,3-diamine |

TABLE 1-continued

| Molecule code | Chemical formula | Nomenclature |
|---|---|---|
| C78 | | N'-(10,11-dimethyl-11H-benzo[g]pyrido[4,3-b]indol-7-yl)-N,N-diethyl-propane-1,3-diamine |
| C79 | | N'-(7,8-dimethyl-7H-benzo[e]pyrido[4,3-b]indol-11-yl)-N,N-dimethyl-propane-1,3-diamine |
| C80 | | N,N-dimethyl-N'-(10-methyl-11H-benzo[g]pyrido[4,3-b]indol-7-yl)-propane-1,3-diamine |
| C81 | | 7-(3-diethylamino-propylamino)-10,11-dimethyl-11H-benzo[g]pyrido[4,3-b]indol-3-ol |
| C82 | | N,N-diethyl-N'-(10-methyl-11H-benzo[g]pyrido[4,3-b]indol-7-yl)-propane-1,3-diamine |
| C83 | | 4-methoxy-10-methyl-11H-benzo[g]pyrido[4,3-b]indol-7-ylamine |

TABLE 1-continued

| Molecule code | Chemical formula | Nomenclature |
| --- | --- | --- |
| C84 | | N,N-diethyl-N'-(3-methoxy-10-methyl-11H-benzo[g]pyrido[4,3-b]indol-7-yl)-propane-1,3-diamine |
| C85 | | N'-(4-methoxy-10,11-dimethyl-11H-benzo[g]pyrido[4,3-b]indol-7-yl)-N,N-dimethyl-propane-1,3-diamine |
| C86 | | 7-(3-(dimethylamino-propylamino)-10,11-dimethyl-11H-benzo[g]pyrido[4,3-b]indol-4-ol |
| C87 | | N,N-dimethyl-N'-(8-methyl-7H-benzo[e]pyrido[4,3-b]indol-11-yl)-propane-1,3-diamine |

TABLE 1-continued

| Molecule code | Chemical formula | Nomenclature |
| --- | --- | --- |
| C88 | | 11-(3-dimethylamino-2-methyl-propylamino)-8-methyl-7H-benzo[e]pyrido[4,3-b]indol-3-ol |
| C89 | | N-(3-methoxy-8-methyl-7H-benzo[e]pyrido[4,3-b]indol-11-yl)-propane-1,3-diamine |
| C90 | | 11-(3-amino-propylamino)-8-methyl-7H-benzo[e]pyrido[4,3-b]indol-3-ol |
| C91 | | N-(3-methoxy-10-methyl-11H-benzo[g]pyrido[4,3-b]indol-7-yl)-propane-1,3-diamine |

TABLE 1-continued
| Molecule code | Chemical formula | Nomenclature |
|---|---|---|
| C92 | 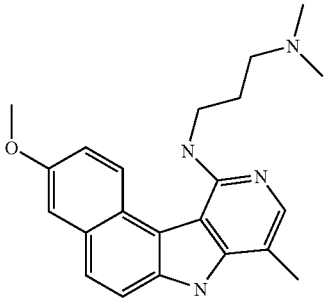 | N'-(3-methoxy-8-methyl-7H-benzo[e]pyrido[4,3-b]indol-11-yl)-N,N-dimethyl-propane-1,3-diamine |
| C93 | 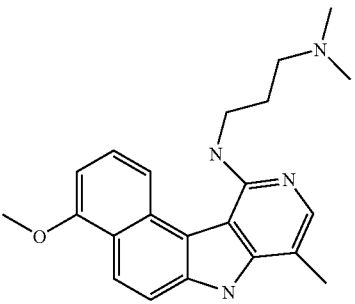 | N'-(4-methoxy-8-methyl-7H-benzo[e]pyrido[4,3-b]indol-11-yl)-N,N-dimethyl-propane-1,3-diamine |
| C94 | 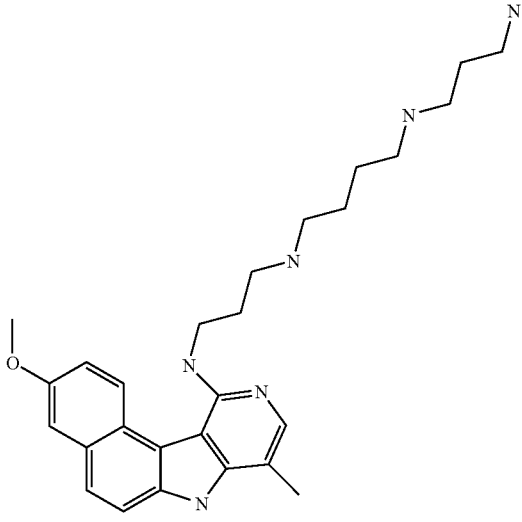 | N-(3-amino-propyl)N'-[3-(3-methoxy-8-methyl-7H-benzo[e]pyrido[4,3-b]indol-11-ylamino)-propyl]butane-1,4-diamine |
| C95 | 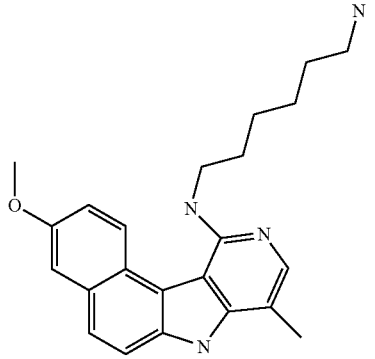 | N-(3-methoxy-8-methyl-7H-benzo[e]pyrido[4,3-b]indol-11-yl)-hexane-1,6-diamine |

TABLE 1-continued

| Molecule code | Chemical formula | Nomenclature |
| --- | --- | --- |
| C96 | | N-[3-(3-methoxy-10-methyl-11H-benzo[g]pyrido [4,3-b]indol-7-ylamino)-propyl[-propane-1,3-diamine |
| C97 | | N-[3-(3-methoxy-10-methyl-11H-benzo[g]pyrido[4,3-b]indol-7-ylamino)-propyl]-N-methyl-propane-1,3-diamine |
| C98 | | N-[3-(3-methoxy-8-methyl-7H-benzo[e]pyrido[4,3-b]indol-11-ylamino)-propyl]-propane-1,3-diamine |
| C99 | | N-(5,6-dimethyl-5H-pyrido[3'4':4,5]pyrrolo[2,3-g]isoquinolin-10-yl)-N'-ethyl-propane-1,3-diamine |

TABLE 1-continued

| Molecule code | Chemical formula | Nomenclature |
|---|---|---|
| C100 | | 6-methyl-5H-pyrido[3',4':4,5]pyrrolo[2,3-g]isoquinolin-10-yl-amine |

TABLE 2

| Molecule code | Chemical formula | Nomenclature |
|---|---|---|
| A | | 6-(2-Dimethylamino-ethylamino)-benzo[c]phenanthridin-3-ol |
| B | | 1-(3-Dimethylamino-propylamino)-5-methyl-naphtho[2,3-g]isoquinoline-6,11-dione |
| D | | 8-Pyrrolidin-1-yl-[1,2,4]triazolo[4,3-a]pyrazine |
| E | | 4-Chloro-2-methyl-5,6,7,8,9,10-hexahydro-3,10-diaza-benzo[a]azulene |
| F | | 8-Hydroxy-2,3,4,9-tetrahydro-carbazol-1-one |

TABLE 2-continued

| Molecule code | Chemical formula | Nomenclature |
|---|---|---|
| G | | N-(2,4-Dinitro-phenyl)-N'-(2-methyl-furan-3-ylmethylene)-hydrazine |
| H | | 5,8-Dimethyl-9H-carbazol-3-ol |
| I | | 5-Methoxy-4-methyl-4a,5-dihydro-2H-isoquinolin-1-one |
| J | | 8-Hydroxy-1-methyl-benzo[h]quinolinium |
| K | | 6-Methyl-5H-pyrido[4,3-b]indole-7-carbaldehyde |

Table 1 represents the compounds according to the invention and Table 2 represents compounds tested having a chemical structure different from the compounds according to the invention.

The first type of pre-messenger corresponds to MINX derived from an adenovirus transcript for which splicing is constitutive (Zillmann, M. et al. (1988), Gel electrophoretic isolation of splicing complexes containing U1 small nuclear ribonucleoprotein particles. Mol. Cell Biol. 8, 814-821). This pre-messenger is obtained in radioactive form by transcription in vitro according to a protocol provided by Promega using 1 μg of linearized plasmid, 20 units of SP6 polymerase and 5 μM [α-32P]UTP in a reaction volume of 25 μl.

50 fmol of this transcript were used for standard splicing reactions containing in 20 μl: 10 mM triethanolamine pH 7.9; 50 mM KCl, 0.1 mM EDTA; 10% glycerol; 0.5 mM DTT; 20 mM creatine phosphate; 2.5 mM ATP; 2.5 nM $MgCl_2$ and 6% polyvinylalcohol. The reactions were left to incubate for 1 h at 30° C.

To test the effect of the compounds according to the invention, 1 μl of the suitable dilution of each compound was added at the beginning of the reaction in the form of a soluble solution in 10% DMSO.

The RNAs produced during the splicing reaction were extracted, analyzed on a 7% polyacrylamide denaturing gel then revealed by autoradiography. An example of inhibition of MINX transcript splicing obtained with 10 μM of compound $C_2$ (lane 4) is presented in FIG. 1.

The second type of M3S1 pre-messenger is derived from the human beta-globulin gene (Labourier, E. et al. (1999), Antagonism between RSF1 and SR proteins for both splice-site recognition in vitro and Drosophila development. Genes Dev. 13, 740-753) and its splicing is strictly dependent on an auxiliary ESE sequence recognized specifically by the SR ASF/SF2 protein. Conditions for the transcription, splicing and analysis of this pre-messenger's products are identical to those used for the MINX pre-messenger.

Figure 2:
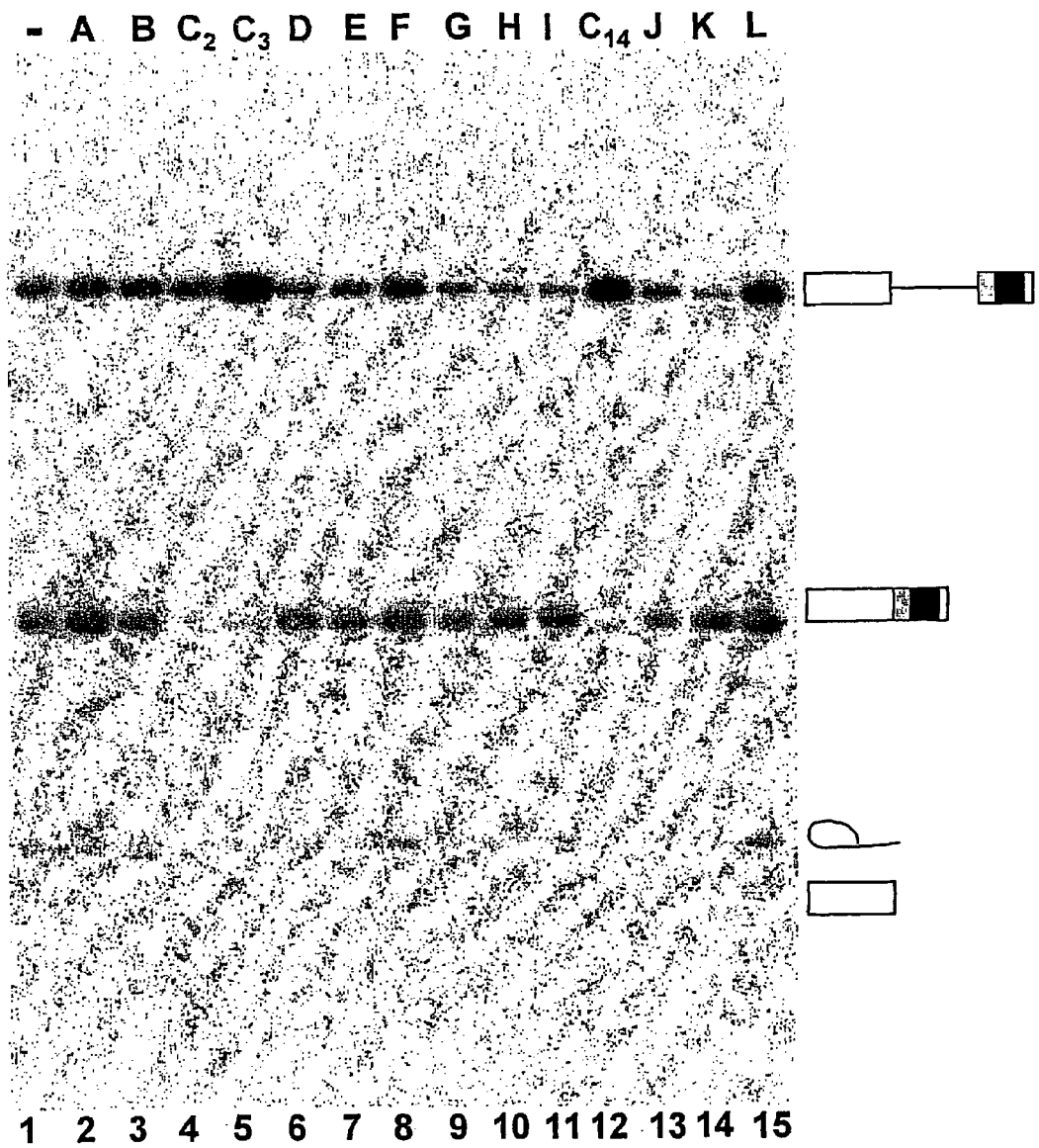
FIG. 2: Analysis of the splicing products of M3S1 pre-messenger RNA obtained in vitro in the presence of various compounds. The structure of the various splicing products is indicated. The rectangles are the exons. The black part of the rectangle represents the ESE. The line representing the intron is in linear or in lasso (*) form.

An example of the M3S1 splicing inhibition obtained with 10 μM of compounds $C_2$, $C_3$ and $C_{14}$ (lanes 4, 5 and 12) is presented in FIG. 2.

The activity of the products has also been tested in splicing-complex formation reactions in vitro (FIG. 3) as described in Pilch B. et al. (Specific inhibition of serine- and arginine-rich splicing factors, phosphorylation, spliceosome assembly, and splicing by the antitumor drug NB-506. Cancer Res. 2001. 61, 6876-6884).

Figure 1:
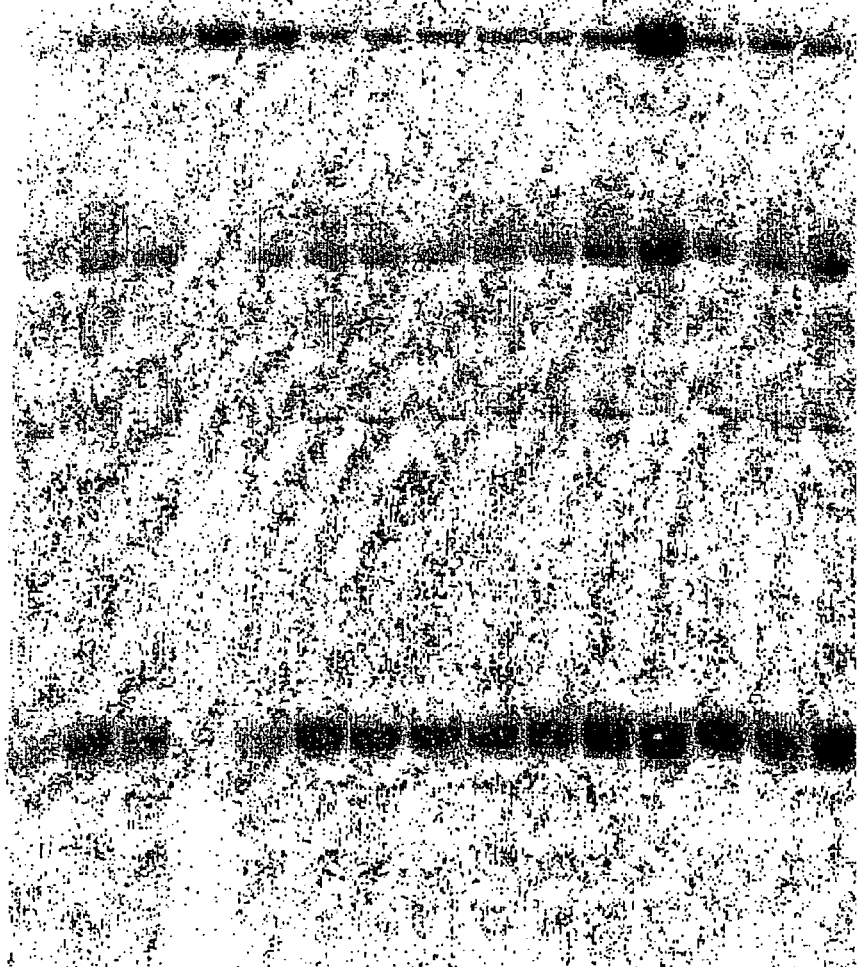
FIG. 1: Analysis of the splicing products of MINX pre-messenger RNA obtained in vitro in the presence of various compounds. The structure of the various splicing products is indicated. The line representing the intron is in linear or in lasso (*) form. The rectangles represent the two MINX exons.

M3S1 transcript splicing reactions in the presence of various compounds according to the invention performed under the same conditions as those described for FIG. 1 are stopped after 30 minutes of incubation by the addition of heparin and glycerol at a final concentration of 1 mg/ml and 15%, respectively. The splicing complexes are separated on a non-denaturing 5% acrylamide gel and are revealed by autoradiography.

Figure 3:
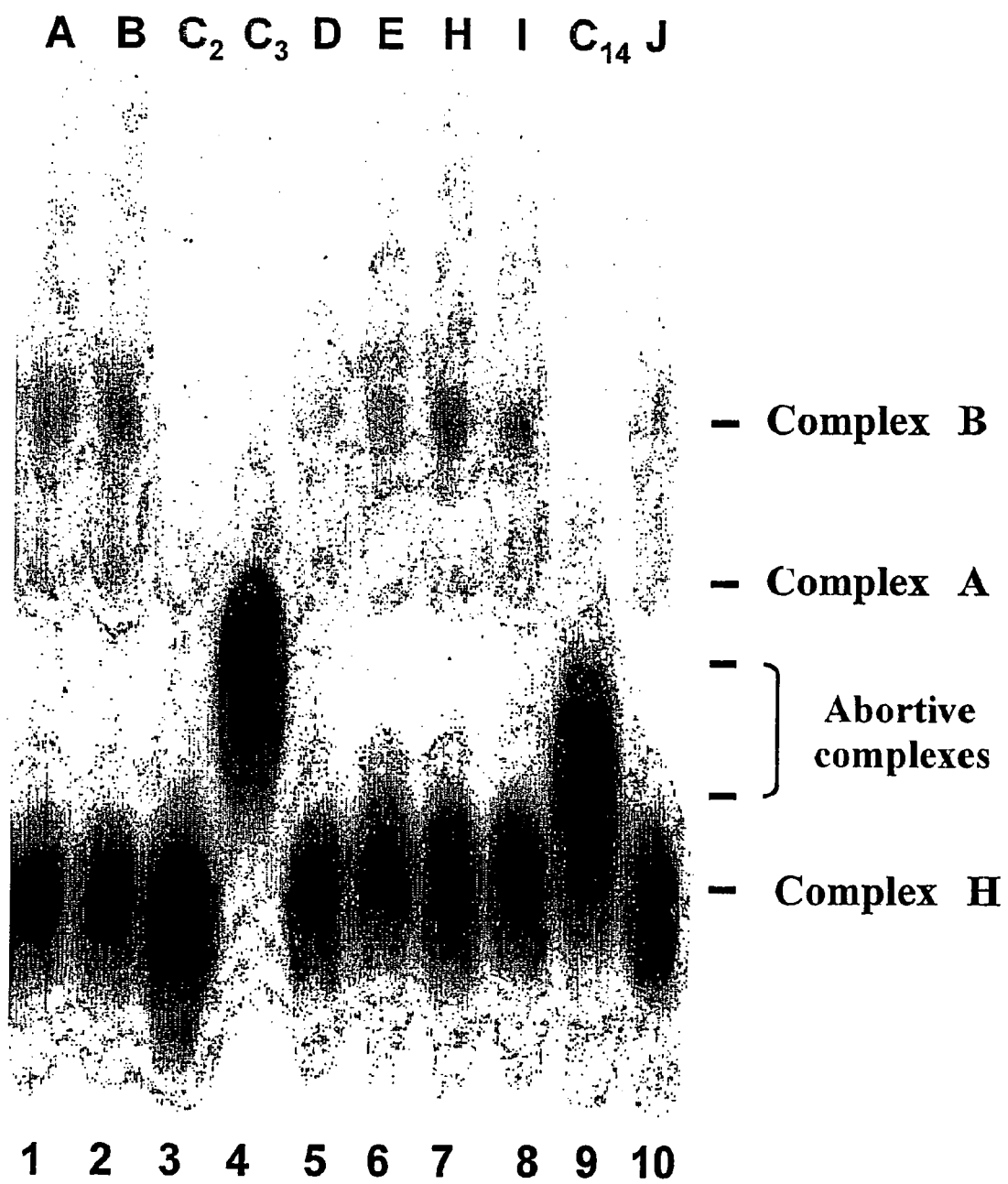
FIG. 3: Analysis of the formation of splicing complexes on M3S1 pre-messenger RNA in the presence of various compounds.

FIG. 3 shows an example of inhibition of the formation of splicing complexes A and B to the detriment of the appearance of abortive complexes for compounds $C_2$, $C_3$ and $C_{14}$ (lanes 3, 4 and 9), used at a concentration of 50 μM.

All of the compounds represented in Table 1 are capable of inhibiting the formation of M3S1 transcript splicing complexes at concentrations ranging between 10 μM and 50 μM.

EXAMPLE 2

In Vivo Inhibition of the ESE-dependent Splicing of GFP (Green Fluorescent Protein) mRNA In order to test the efficiency of indole derivatives ex vivo, fibroblast HeLa cell lines were established stably expressing a transgene corresponding to GFP whose sequence was interrupted by an ESE sequence flanked by two identical introns of the human beta-globulin gene described in Example 1 (see FIG. 5A).

To detect the messenger RNAs arising from the splicing of this gene, the RT-PCR technique was used with primers in the GFP sequence on each side of the ESE and the PCR products were analyzed on agarose gel.

In almost all the lines established, a single fragment of 250 base pairs (bp) was amplified by PCR (FIG. 5A, lanes 2 and 3) and it corresponds to an RNA messenger which included the ESE between the two GFP sequences.

The result indicates that the ESE has a dominant effect and that the RNA messenger produced after splicing contains the two parts of the GFP interrupted by the ESE (FIG. 5A, GFP-ESE-GFP).

Conversely, the treatment of cells by indole derivatives $C_{28}$ (lane 4) and $C_{14}$ (lane 5) revealed a fragment of 194 bp, to the detriment of the 250 bp fragment, which no longer contained an ESE sequence between the GFP sequences, thus demonstrating that certain indole derivatives according to the invention can suppress the effect of ESEs in cells.

Certain compounds represented in Table 1 were tested with a concentration at least equal to 1 μM and proved to be ineffective in this test at this concentration as they did not induce a change in the splicing profile of the GFP-ESE transgene.

Nevertheless, it should be noted that the ESE of the GFP-ESE transgene used in the experiments described above is specific to the protein SR SF2/ASF and it is quite probable that the other compounds according to the invention represented in Table 1 are capable of influencing the splicing controlled by other types of ESEs specific to other SR proteins (SC35, 9G8, SRp55, SRp40 or SRp75). This hypothesis is supported by the in vitro splicing results represented in Table 3 below which indicate that compounds C16, C19, C42, C50, C57, C76, C77, C78, C79, C80, C82, C85, C87, C88, C93 and C95 inhibit the activity of the SRp55 protein specifically. The present invention thus encompasses the use of indole-derived compounds for the treatment of genetic diseases resulting from modification of the splicing processes, either consecutive or dependent on ESE, ISE, ESS or ISS regulatory sequences.

TABLE 3

| | SF2 | SRp55 | SC35 |
|---|---|---|---|
| C1 | ++++ | ++++ | ++++ |
| C2 | ++++ | -- | ++++ |
| C3 | ++++ | ---- | ++++ |
| C4 | ---- | ---- | ---- |
| C5 | ++++ | ---- | ---- |
| C6 | ---- | ---- | ---- |
| C7 | ++++ | ---- | ---- |
| C8 | ++++ | ---- | ++++ |
| C9 | ++++ | ---- | ---- |
| C10 | ---- | ---- | ---- |
| C11 | +/- | ---- | ++++ |
| C12 | ++++ | ++++ | ++++ |
| C13 | ++++ | / | ---- |
| C14 | ++++ | ++++ | ---- |
| C15 | ---- | ---- | ++++ |
| C16 | +/- | ++++ | ++++ |
| C17 | ---- | ---- | ++++ |
| C18 | ---- | ---- | ++++ |
| C19 | +/- | ++++ | ++++ |
| C20 | ---- | ---- | ---- |
| C21 | ++++ | ---- | ++++ |
| C22 | ---- | ---- | ----- |
| C23 | ---- | ---- | ----- |
| C24 | ---- | ---- | ----- |
| C25 | ---- | ---- | ++++ |
| C26 | ++++ | ---- | ++++ |
| C27 | ---- | ---- | ++++ |
| C28 | +/- | ---- | / |
| C29 | ++++ | ++++ | / |
| C30 | ++++ | ++++ | / |
| C31 | ++++ | ++++ | / |
| C32 | ++++ | ++++ | / |
| C33 | ++++ | ++++ | / |
| C34 | ++++ | ---- | / |
| C35 | ++++ | ---- | / |
| C36 | ++++ | ++++ | / |
| C37 | ++++ | ++++ | / |
| C38 | ++++ | ++++ | / |
| C39 | ++++ | ++++ | / |
| C40 | ++++ | ++++ | / |
| C41 | ++++ | ++++ | / |
| C42 | ---- | +++ | / |
| C43 | ++++ | ++++ | / |
| C44 | ++++ | ---- | / |
| C45 | ++++ | ---- | / |
| C46 | ++++ | ++++ | / |
| C47 | ++++ | --- | / |
| C48 | ++++ | ++++ | / |
| C49 | ++++ | ++++ | / |
| C50 | ----- | ++++ | / |
| C51 | ++++ | --- | / |
| C52 | ++++ | ++++ | / |
| C53 | ++++ | ++++ | / |
| C54 | ++++ | +++ | / |
| C55 | +/- | +++ | / |
| C56 | ++++ | +++ | / |
| C57 | ----- | ++++ | / |
| C58 | ++++ | --- | / |
| C59 | +++++ | ++++ | / |
| C60 | +++++ | ++++ | / |
| C61 | +++++ | ++++ | / |
| C62 | +++++ | ++++ | / |
| C63 | ++++ | ++++ | ++++ |
| C64 | ++++ | ++++ | / |
| C65 | ++++ | ++++ | / |
| C66 | ++++ | ++++ | / |
| C67 | ++++ | ++++ | / |
| C68 | +/- | ---- | / |
| C69 | ++++ | ++ | / |
| C70 | +/ | ---- | / |
| C71 | +/ | ---- | / |
| C72 | +/ | ---- | / |
| C73 | ++++ | ---- | / |
| C74 | ++++ | ++ | / |
| C75 | ++++ | +++ | / |
| C76 | +/- | +++ | / |
| C77 | ---- | + | / |
| C78 | ---- | + | / |

TABLE 3-continued

| | SF2 | SRp55 | SC35 |
|---|---|---|---|
| C79 | ---- | ++ | / |
| C80 | +/- | ++ | / |
| C81 | ++++ | +++ | / |
| C82 | ---- | ++ | / |
| C83 | ++++ | ---- | / |
| C84 | ++++ | ++++ | / |
| C85 | +/- | + | / |
| C86 | ++++ | ++ | / |
| C87 | +/- | ++ | / |
| C88 | +/- | ++ | / |
| C89 | ++++ | +++ | / |
| C90 | ++++ | --- | / |
| C91 | ++++ | --- | / |
| C92 | ++++ | --- | / |
| C93 | +/- | ++++ | / |
| C94 | ++++ | ++++ | / |
| C95 | +/- | ++++ | / |
| C96 | ++++ | ++++ | / |
| C97 | ++++ | --- | / |
| C98 | ++++ | ++ | / |
| C99 | ++++ | ---- | / |
| C100 | ++++ | ---- | / |

EXAMPLE 3

Figure 4:
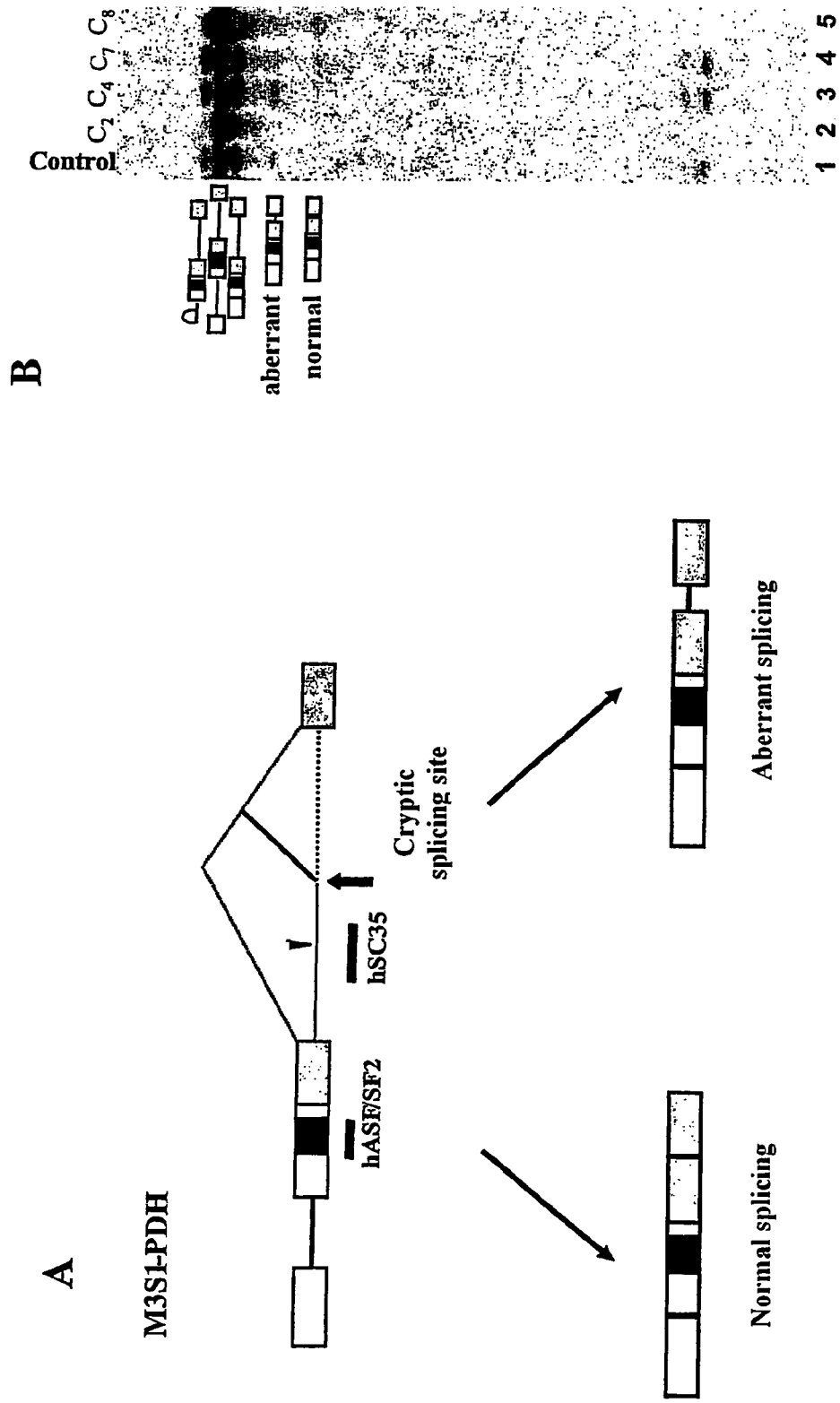
FIG. 4: (A) Structure of two types of transcripts produced by splicing exon 7-intron 7-exon 8 of the gene coding for the E1α sub-unit of mutated pyruvate dehydrogenase.

In Vivo Inhibition of the ESE-dependent Splicing of Pyruvate Dehydrogenase E1α Subunit mRNA In order to demonstrate the selectivity of the action on ESE sequences by the compounds according to the invention, it was decided to use another model substrate containing two introns whose splicing depends on two different ESE sequences. In this substrate the sequences corresponding to exon 7-intron 7-exon 8 of the gene coding for the pyruvate dehydrogenase E1α subunit (PDH E1α) are inserted downstream from the M3S1 sequence (M3S1-PDH, see FIG. 4A). Intron 7 of this transcript contains a point mutation which creates a high affinity SR hSC35 protein binding site. This mutation, which causes the loss of PDH E1α expression in patients suffering from Leigh syndrome (an encephalopathy in children), leads to the appearance of a cryptic site 46 nucleotides downstream from the authentic 5' splicing site (FIG. 4A). This substrate, likely to give rise to two products, one with and one without the 46 nucleotides of PDH intron 7, is ideal for determining the specificity of the compounds with respect to the various ESE sequences present within the same transcript. Compound $C_2$, which inhibits M3S1, abolishes M3S1-PDH splicing completely (FIG. 4B, compare lanes 1 and 2). Inhibition of M3S1-PDH is also observed with compound $C_8$ (FIG. 4B, lane 5), indicating that the ESE sequence contained in M3S1 is required to initiate the first splicing event serving to eliminate intron 1. Conversely, compound $C_4$, inactive on M3S1, has no effect (FIG. 4B, lane 3).

However, the screening of other compounds that do not modify M3S1 splicing revealed in a surprising way that compound $C_7$ blocks the formation of RNA species arising from PDH splicing that include the 46 nucleotides of intron 7, but has no effect on those derivatives from normal PDH splicing (FIG. 4B, lane 4). Compound $C_7$ is thus an excellent inhibitor of defective splicing that is dependent on hSC35 ESE, but not on authentic splicing. This compound can thus be envisaged for treating patients suffering from this encephalopathy.

EXAMPLE 4

Inhibition of HIV Multiplication by the Compounds of the Invention

The AIDS virus, like practically all retroviruses, has recourse to alternative splicing to express the genes essential to its replication. Indeed, the version of the virus that integrates itself into the genome of human cells is transcribed in the form of a single precursor which, by alternative splicing, generates 40 different RNA messengers coding for viral proteins essential to its replication (Furtado et al., 1991. Analysis of alternatively spliced human immunodeficiency virus type-1 mRNA species, one of which encodes a novel tat-env fusion protein. Virology, 185: 258-270; Purcell and Martin, 1993. Alternative splicing of human immunodeficiency virus type 1 mRNA modulates viral protein expression, replication, and infectivity. J. Virol., 67: 6365-78). These splicing events are controlled by several ESE regulatory sequences, some of which are localized downstream from the splicing sites responsible for the expression of key viral replication proteins such as tat, rev, vpu, env and nef (Caputi et al., 2004. A bidirectional SF2/ASF- and SRp40-dependent splicing enhancer regulates human immunodeficiency virus type 1 rev, env, vpu, and nef gene expression. J. Virol. 78: 6517-26; Pongoski et al., 2002. Positive and negative modulation of human immunodeficiency virus type 1 Rev function by cis and trans regulators of viral RNA splicing. J. Virol. 76: 5108-20).

Since the compounds according to the invention inhibit the use of ESE-sequence-dependent splicing sites, their effectiveness to block viral replication was tested. To this end, human lymphocyte cell line U1, which is chronically infected by HIV (Folks et al., 1988. Characterization of a promonocyte clone chronically infected with HIV and inducible by 13-phorbol-12-myristate acetate. J. Immunol., 140: 1117-1122) and which produces large quantities of virus after stimulation by PMA (phorbol myristate acetate), was used. As a result, this cell line constitutes an excellent model to mimic the transition between the latency phase and the viral production phase observed in patients infected by HIV.

The results of this experiment are presented in FIG. 6 in which U1 cells ($5\times10^5$) were treated with 50 nM of PMA in the absence (FIG. 6, lane 1) or in the presence of 2.5 μM of compounds $C_{47}$, $C_{97}$, $C_{58}$, $C_{57}$, $C_{92}$, $C_{91}$, $C_{90}$, $C_{83}$, $C_{73}$, $C_{34}$, $C_{51}$, $C_{45}$, $C_{13}$, $C_{10}$, $C_{44}$, $C_6$, $C_7$, $C_{41}$, $C_{50}$, $C_{32}$, $C_2$, $C_1$, $C_{29}$, $C_{35}$ and $C_{99}$ (FIG. 6, lanes 3-27, respectively). After 24 h of treatment, the virus's transcripts were amplified by RT-PCR using specific VIH, BSS and SJ4.7A primers (Jacquenet et al., 2001, A second exon splicing silencer within human immunodeficiency virus type 1 tat exon 2 represses splicing of Tat mRNA and binds protein hnRNP. H. J. Biol. Chem. 276: 40464-75) and a radioactive tracer (α-32P) CTP. The amplification products were analyzed on a 7% polyacrylamide denaturing gel and then revealed by autoradiography. Among the 29 compounds tested, compounds $C_{47}$, $C_{97}$, $C_{57}$, $C_{92}$, $C_{91}$, $C_{83}$, $C_{51}$, $C_{13}$, $C_{10}$, $C_{44}$, $C_{41}$, $C_{50}$, $C_{32}$, $C_2$, $C_1$, $C_{29}$, $C_{35}$ and $C_{99}$ (lanes 3, 4, 6-8, 10, 13, 15-17, 20-27, respectively) were shown to be excellent inhibitors of HIV multiplication because no amplification of the virus was detected in the cells treated by these compounds.

EXAMPLE 5

10-Chloro-2,6-dimethyl-2H-pyrido[3',4':4,5]pyrrolo [2,3-g]isoquinoline

50% NaH (90 mg) is added to the solution of 10-chloro-6-methyl-5H-pyrido[3',4':4,5]pyrrolo[2,3-g]isoquinoline (400 mg; product known, already published) in N,N-dimethylacetamide (20 ml) cooled to −10° C. The mixture is stirred for 30 min then $CH_3I$ (0.11 ml) is introduced and the mixture is stirred again at −10° C. for 2.5 h. Water and $CH_2Cl_2$ are added and the organic phase is separated, dried ($MgSO_4$) and dry evaporated. The residue obtained is chromatographed on a silica column by eluting successively with $CH_2Cl_2$-EtOH (9:1 v/v) then EtOH-NEt$_3$ (95:5 v/v) to yield respectively 10-chloro-5,6-dimethyl-5H-pyrido[3',4':4,5]pyrrolo[2,3-g]isoquinoline (66 mg, 16% yield) and the expected 10-chloro-2,6-dimethyl-2H-pyrido[3',4':4,5]pyrrolo[2,3-g]isoquinoline (138 mg, 32% yield) in the form of yellow microcrystals (point melting>260° C.). NMR in agreement.

EXAMPLE 6

(9-Methoxy-5-methyl-6H-pyrido[4,3-b]carbazol-1-yl)-(2,2,6,6-tetramethyl-piperidin-4-yl)-amine The mixture of 1-chloro-9-methoxy-5-methyl-6H-pyrido[4,3-b]carbazole (1.0 g; product known, already published) and 4-amino-2,2,6,6-tetramethylpiperidin (1.0 g) is heated at 150° C. for 21 h. Excess amino is eliminated by evaporation under reduced pressure. Water is added to the residue obtained to form a solid. This solid is filtered, washed with water, then recrystallized from xylene to yield the expected (9-methoxy-5-methyl-6H-pyrido[4,3-b]carbazol-1-yl)-(2,2,6,6-tetramethyl-piperidin-4-yl)-amine (1.0 g, 71% yield) in the form of yellow microcrystals (melting point: 223-225° C.). NMR in agreement.

EXAMPLE 7

N-ethyl-N-[3-9-methoxy-5,11-dimethyl-6H-pyrido[4,3-b]carbazol-1-ylamino)-propyl]-succinamic acid A solution of 100 mg of succinic anhydride (1 mM) and 376 mg (1 mM) of N-ethyl-(9-methoxy-5,11-dimethyl-6H-pyrido[4,3-b]carbazol-1-yl)-propane-1,3-diamine in 100 ml of dry toluene was brought to reflux for 5 h. The precipitate obtained after cooling was dried and recrystallized in acetone. 270 mg (54.6%) of the desired product were obtained in the form of a solid (F~150°). Centesimal analysis for $C_{27}H_{32}N_4O_4+H_2O$; Calc.: C, 65.57; H, 6.93; N, 11.33 Exp.: C, 65.18; H, 6.88; N, 10.95. NMR and MS in agreement.

EXAMPLE 8

N-ethyl-N-[3-(6-methyl-5H-pyrido[3',4':4,5]pyrrolo[2,3-g]isoquinolin-10-ylamino)-propyl]-succinamic acid A solution of 75 mg of succinic anhydride (0.75 mM) and 250 mg (0.75 mM) of N-ethyl-N'-(6-methyl-5H-pyrido[3',4':4,5]pyrrolo[2,3-g]isoquinolin-10-yl)propane-1,3-diamine in 80 ml of dry toluene was brought to reflux for 4 h. The precipitate obtained after cooling was dried and recrystallized with acetone. 240 mg (65.6%) was obtained in the form of solid (F~150°). Centesimal analysis for $C_{24}H_{27}N_5O_3+3H_2O$; Calc.: C, 59.12; H, 6.82; N, 14.37; Exp.; C, 59.14; H, 6.88; N, 14.17. NMR and MS in agreement.

EXAMPLE 9

9-methoxy-5-methyl-4,6-dihydro-3H-pyrido[4,3-b]carbazole

A suspension of 1.5 g of 2-(-6-methoxy-1-methyl-9H-carbazol-2yl)-ethylamine in 15 ml of ethyl formate is brought to reflux for 20 h. The solution obtained is concentrated under a vacuum and the paste obtained is taken up in dichloromethane. After complete evaporation under reduced pressure, the solid obtained is ground then washed with pentane to yield 1.6 g (98%) of N-formyl intermediate derivative.

1.6 g of this intermediate are dissolved in 120 ml of dry toluene and the mixture is brought to reflux in a tricol flask equipped with a Dean Stark. 12 ml of $POCl_3$ are added dropwise over 10 min and reflux is maintained for 24 h. After cooling and evaporation of the toluene and the $POCl_3$, under reduced pressure, the solid is taken up in 500 ml 2 N HCl and brought to boil. A light insoluble is filtered and, from the cooled solution, the hydrochloride is dried. The aforementioned is taken up in 2 N $NH_4OH$ (up to pH 12). After drying, the dry yellow precipitate yields 1.4 g (92%) of the desired product. NMR in agreement.

EXAMPLE 10

N-(3-amino-propyl)N'-[3-(3-methoxy-8-methyl-7H-benzo[e]pyrido[4,3-b]indole-11-ylamino)-propyl]butane-1,4-diamine The mixture of 11-chloro-8-methyl-3-methoxy-7H-benzo[e]pyrido[4,3-b]indole (210 mg; product known, already published) and spermine (1.0 g) is heated at 170° C. for 18 h. Excess amino is eliminated by evaporation under reduced pressure and the residue obtained is taken up in $CH_2Cl_2$ then washed with water. The organic phase is dried ($MgSO_4$) and dry evaporated. The free base obtained is dissolved in boiling absolute ethanol (15 ml) and then poured into a solution containing maleic acid (410 mg) and ethanol (10 ml). The precipitate obtained is filtered at 20° C., washed with ethanol and dried away from moisture to yield 270 mg (39%) of the expected product's tetramaleate salt. Centesimal analysis for $C_{43}H_{54}N_6O_{17}+2H_2O$; Calc.: C, 53.64; H, 6.03; N, 8.73; Exp.: C, 53.83; H, 6.01; N, 8.79. NMR in agreement.

EXAMPLE 11

N-(3-methoxy-8-methyl-7H-benzo[e]pyrido[4,3-b]indole-11-yl)-hexane-1,6-diamine

The mixture of 11-chloro-8-methyl-3-methoxy-7H-benzo[e]pyrido[4,3-b]indole (360 mg; product known, already published) and hexane-1,6-diamine (5 ml) is heated at 170° C. for 18 h. Excess amino is eliminated by evaporation under reduced pressure and the residue obtained is taken up in $CH_2Cl_2$ then washed with water. The organic phase is dried ($MgSO_4$) and dry evaporated. The free base obtained is dissolved in boiling absolute ethanol (15 ml) and then poured into a solution containing maleic acid (648 mg) and ethanol (10 ml). The precipitate obtained is filtered at 20° C., washed with ethanol and dried away from moisture to yield 700 mg (89%) of the expected product's bimaleate salt. Centesimal analysis for $C_{31}H_{36}N_4O_9+2H_2O$; Calc.: C, 57.76; H, 6.21; N, 8.69; Exp.: C, 58.22; H, 9.91; N, 8.47. NMR in agreement.

EXAMPLE 12

N-[3-(3-methoxy-10-methyl-11H-benzo[g]pyrido[4,3-b]indole-7-ylamino)-propyl]-propane-1,3-diamine The mixture of 7-chloro-10-methyl-3-methoxy-11H-benzo[g]pyrido[4,3-b]indole (335 mg; product known, already published) and N-(3-aminopropyl)-1,3-propanediamine (8 ml) is heated at 170° C. for 18 h. Excess amino is eliminated by evaporation under reduced pressure and the residue obtained is taken up in $CH_2Cl_2$ then washed with water. The organic phase is dried ($MgSO_4$) and dry evaporated. The free base obtained is dissolved in boiling absolute ethanol (15 ml) and then poured into a solution containing maleic acid (620 mg) and ethanol (10 ml). The precipitate obtained is filtered at 20° C., washed with ethanol and dried away from moisture to yield 460 mg (53%) of the expected product's trimaleate salt. Centesimal analysis for $C_{35}H_{41}N_5O_{13}+H_2O$; Calc.: C, 55.48; H, 5.68; N, 9.25 Exp.: C, 55.01; H, 5.68; N, 9.14. NMR in agreement.

EXAMPLE 13

N-[3-(3-methoxy-8-methyl-7H-benzo[e]pyrido[4,3-b]indole-11-ylamino)-propyl]-propane-1,3-diamine The mixture of 11-chloro-8-methyl-3-methoxy-7H-benzo[e]pyrido[4,3-b]indole (290 mg; product known, already published) and N-(3-aminopropyl)-1,3-propanediamine (5 ml) is heated at 170° C. for 30 h. Excess amino is eliminated by evaporation under reduced pressure and the residue obtained is taken up in $CH_2Cl_2$ then washed with water. The organic phase is dried ($MgSO_4$) and dry evaporated. The free base obtained is dissolved in boiling absolute ethanol (15 ml) and then poured into a solution containing maleic acid (620 mg) and ethanol (10 ml). The precipitate obtained is filtered at 20° C., washed with ethanol and dried away from moisture to yield 360 mg (48%) of the expected product's trimaleate salt. Centesimal analysis for $C_{35}H_{41}N_5O_{13}+1.5\ H_2O$; Calc.: C, 54.83; H. 5.74; N, 9.14 Exp.: C, 54.98; H, 5.91; N, 8.76. NMR in agreement.

The invention claimed is:
1. A method of treating a disease related to a pre-messenger RNA splicing process within a cell wherein said disease is Frasier syndrome, frontotemporal dementia related to chromosome 17 (a form of Parkinson's), Leigh syndrome (a type of encephalopathy), atypical cystic fibrosis, a certain neuropathology related to Tau protein mutation, Alzheimer's disease, amyotrophy that influences the SMN (survival motor neuron) gene, depression related to disturbances in serotonin splicing and AIDS, comprising administering to a patient in need thereof a medicine comprising a compound of benzo-indole or pyrido-indole derivative corresponding to the following formula I:

Formula I

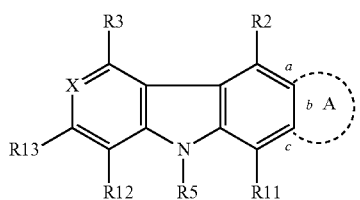

or a pharmaceutically acceptable salt, isomer and/or mixture thereof, wherein
X represents N or N⁺R4 anhydro base,
and ring A, which is in position b corresponds to

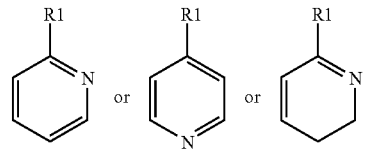

wherein R1 represents
an atom of hydrogen or halogen or a —C=N—OH or —O—C(=O) (CH₃) or —C≡N group, or a —N—R6R7 group, wherein R6 and R7 represent independently of one another
a hydrogen atom,
a saturated or unsaturated ring having C6, optionally containing an atom of nitrogen and possibly substituted by one or more alkyl groups at C1 to C3, or
a linear, branched and/or unsaturated alkyl group having C1 to C13 in which one or more atoms of carbon is optionally substituted by an atom of nitrogen, said alkyl group being optionally substituted by one or more —OH and/or =O groups and/or by a group selected from the following compounds:

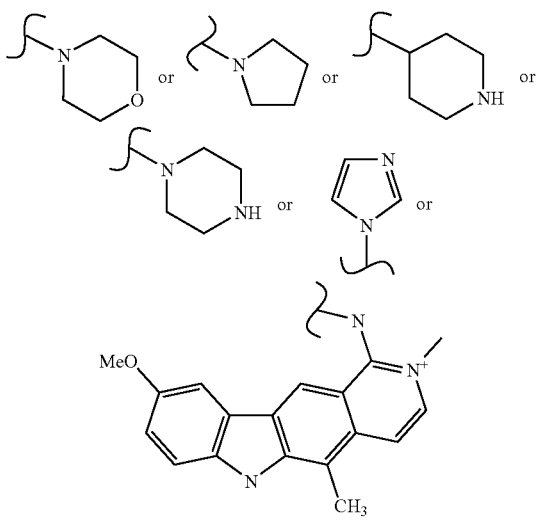

said group being optionally substituted by an alkyl group at C1 to C3 which itself is possibly substituted by an amino group, or a —NH—R8 group
wherein R8 represents an alkyl-N—R9R10 group,
wherein the alkyl group of said alkyl-N—R9R10 group represents a linear or branched group having C1 to C13 optionally unsaturated and/or substituted by one or more alkyl groups at C1 to C3 and/or hydroxyl groups, and
R9 and R10 represent independently of one another a hydrogen atom or an alkyl group having C1 to C4 optionally substituted by one or more hydroxyl and/or oxo groups,
R2 represents a hydrogen atom, a methyl group or a —NH—(CH₂)₃—N(CH₃)₂ group,
R3 represents a hydrogen atom, a halogen atom or a methyl, amino or methoxymethyl group, or said —NH—R8 group,
R4 represents a hydrogen atom, a hydroxyl or alkyl group having C1-C6 or a methoxy group optionally substituted by a phenyl group,
R5 represents a hydrogen atom or a methyl or methoxymethyl group when X represents N or R5 is absent when X represents N⁺R4 anhydro base,
R11 and R12 represent independently of one another a hydrogen atom or an alkyl group having C1-C3 and
R13 represents a hydrogen atom or a methyl group.
2. The method of claim 1, wherein said compound of pyrido-indole derivative is a derivative of pyrido-pyrrolo-isoquinoline of said formula I, wherein X represents N or N⁺R4 anhydro base, and ring A represents

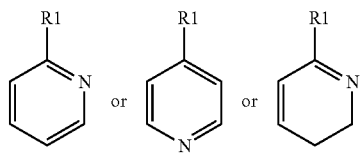

wherein R1 represents a halogen atom, an amino group, said —N—R6R7 or said —NH—R8 group,
R2 represents a hydrogen atom or a methyl group,
R3 represents a hydrogen atom or said NH—R8 group,
R4 represents a hydrogen atom or a methyl group,
R5 represents a hydrogen atom or a methyl group when X represents N or R5 is absent when X represents said N⁺R4 anhydro base, and
R11 represents a hydrogen atom or a methyl group.

3. The method of claim 1, wherein said compound is selected from a group consisting of:
  10-chloro-2,6-dimethyl-2H-pyrido[3',4':4,5]pyrrolo[2,3-g]isoquinoline,
  N'-(6,11-dimethyl-5H-pyrido[3',4':4,5]pyrrolo[2,3-g]isoquinolin-10-yl)-N,N-dimethyl-propane-1,3-diamine,
  N,N-dimethyl-N'-(6-methyl-5H-pyrido[3',4':4,5]pyrrolo[2,3-g]isoquinolin-10-yl)-propane-1,3-diamine,
  N-ethyl-N-[3-(6-methyl-5H-pyrido[3',4':4,5]pyrrolo[2,3-g]isoquinolin-10-ylamino)-propyl]-succinamic acid,
  2-{(2-hydroxy-ethyl)-[3-(6-methyl-5H-pyrido[3',4':4,5]pyrrolo[2,3-g]isoquinolin-10-ylamino}propyl]-amino-ethanol,
  N-(6-methyl-5H-pyrido[3',4':4,5]pyrrolo[2,3-g]isoquinolin-10-yl)-propane-1,3-diamine,
  N-3-(5,6-dimethyl-5H-pyrido[3',4':4,5]pyrrolo[2,3-g]isoquinolin-10-yl)-N, N-1-diethyl-butane-1,3-diamine,
  N-(6,11-dimethyl-5H-pyrido[3',4':4,5]pyrrolo[2,3-g]isoquinolin-10-yl)-N'-ethyl-propane-1,3-diamine,
  N'-(5,6-dimethyl-5H-pyrido[3',4':4,5]pyrrolo[2,3-g]isoquinolin-10-yl)-N,N-dimethyl-propane-1,3-diamine,
  N-(5,6-dimethyl-5H-pyrido[3',4':4,5]pyrrolo[2,3-g]isoquinolin-10-yl)-N'-ethyl-propane-1,3-diamine,
  (3-imidazol-1-yl-propyl)-(6-methyl-5H-pyrido[3',4':4,5]pyrrolo[2,3-g]isoquinolin-10-yl)-amine,
  N-N,diethyl-N'-(6-methyl-5H-pyrido[3',4':4,5]pyrrolo[2,3-g]isoquinolin-10-yl)-propane-1,3-diamine,
  N-1,N-10-Bis-(3-diethylamino-propyl)-3,6-dimethyl-5H-pyrido[3',4':4,5]pyrrolo[2,3-g]isoquinoline-1,10-diamine,
  N,N-dimethyl-N'-(10,11-dimethyl-10H-pyrido[3',4':4,5]pyrrolo[3,2-g]quinoline)4-yl-propane-1,3-diamine,
  N,N-diethyl-N'-(10,11-dimethyl-10H-pyrido[3',4':4,5]pyrrolo[3,2-]quinoline)-4-yl-propane-1,3-diamine,
  N,N-diethyl-N'-(11-methyl-10H-pyrido[3',4':4,5]pyrrolo[3,2-g]quinoline)-4-yl-propane-1,3-diamine,
  N,N-dimethyl-N'-(11-methyl-10H-pyrido[3',4':4,5]pyrrolo[3,2-g]quinoline)-4-yl-propane-1,3-diamine,
  N-(5,6-dimethyl-5H-pyrido[3',4':4,5]pyrrolo[2,3-g]isoquinolin-10-yl)-N'-ethyl-propane-1,3-diamine, and
  6-methyl-5H-pyrido[3',4':4,5]pyrrolo[2,3-g]isoquinolin-10-yl-amine.

4. The method as in claim 1 wherein said compound is selected from a group consisting of:
  10-chloro-2,6-dimethyl-2H-pyrido[3',4':4,5]pyrrolo[2,3-g]isoquinoline,
  N'-(6,11-dimethyl-5H-pyrido[3',4':4,5]pyrrolo[2,3-g]isoquinolin-10-yl)-N,N-dimethyl-propane-1,3-diamine,
  N,N-dimethyl-N'-(6-methyl-5H-pyrido[3',4':4,5]pyrrolo[2,3-g]isoquinolin-10-yl)-propane-1,3-diamine,
  N-ethyl-N-[3-(6-methyl-5H-pyrido[3',4':4,5]pyrrolo[2,3-g]isoquinolin-10-ylamino)-propyl]-succinamic acid,
  2-{(2-hydroxy-ethyl)-[3-(6-methyl-5H-pyrido[3',4':4,5]pyrrolo[2,3-g]isoquinolin-10-ylaminol}propyl]-aminoethanol,
  N,N-diethyl-N'-(6-methyl-5H-pyrido[3',4':4,5]pyrrolo[2,3-g]isoquinolin-10-yl)-ethane-1,2-diamine,
  N-(6-methyl-5H-pyrido[3',4':4,5]pyrrolo[2,3-g]isoquinolin-10-yl)-propane-1,3-diamine,
  N-3-(5,6-dimethyl-5H-pyrido[3',4':4,5]pyrrolo[2,3-g]isoquinolin-10-yl)-N, N-1-diethyl-butane-1,3-diamine,
  N-(6,11-dimethyl-5H-pyrido[3',4':4,5]pyrrolo[2,3-g]isoquinolin-10-yl)-N'-ethyl-propane-1,3-diamine,
  N'-(5)6-dimethyl-5H-pyrido[3',4':4,5]pyrrolo[2,3-g]isoquinolin-10-yl)-N,N-dimethyl-propane-1,3-diamine,
  N-(5,6-dimethyl-5H-pyrido[3',4':4,5]pyrrolo[2,3g]isoquinolin-10-yl)-N'-ethyl-propane-1,3-diamine,
  (3-imidazol-1-yl-propyl)-(6-methyl-5H-pyrido[3',4':4,5]pyrrolo[2,3-g]isoquinolin-10-yl)-amine,
  N-N-diethyl-N'-(6-methyl-5H-pyrido[3',4':4,5]pyrrolo[2,3-g]isoquinolin-10-yl)-propane-1,3-diamine,
  N-1,N-10-Bis-(3-diethylamino-propyl)-3,6-dimethyl-5H-pyrido[3',4':4,5]pyrrolo[2,3-g]isoquinoline-1,10-diamine,
  N,N-dimethyl-N'-(10,11-dimethyl-10H-pyrido[3',4':4,5]pyrrolo[3,2-g]quinoline)4-yl-propane-1,3-diamine,
  N,N-diethyl-N'-(10,11-dimethyl-10H-pyrido[3',4':4,5]pyrrolo[3,2-]quinoline)-4-yl-propane-1,3-diamine,
  N,N-diethyl-N'-(11-methyl-10H-pyrido[3',4':4,5]pyrrolo[3,2-g]quinoline)-4-yl-propane-1,3-diamine,
  N,N-dimethyl-N'-(11-methyl-10H-pyrido[3',4':4,5]pyrrolo[3,2-g]quinoline)-4-yl-propane-1,3-diamine,
  N-(5,6-dimethyl-5H-pyrido[3',4':4,5]pyrrolo[2,3-g]isoquinolin-10-yl)-N'-ethyl-propane-1,3-diamine, and
  6-methyl-5H-pyrido[3',4':4,5]pyrrolo[2,3-g]isoquinolin-10-yl-amine.

5. The method of claim 1, wherein said compound is selected from a group consisting of:
  10-chloro-2,6-dimethyl-2H-pyrido[3',4':4,5]pyrrolo[2,3-g]isoquinoline,
  N-ethyl-N-[3-(6-methyl-5H-pyrido[3',4':4,5]pyrrolo[2,3-g]isoquinolin-10-ylamino)-propyl]-succinamic acid,
  N,N-diethyl-N'-(6-methyl-5H-pyrido[3',4':4,5]pyrrolo[2,3-g]isoquinolin-10-yl)-ethane-1,2-diamine,
  N'-(5,6-dimethyl-5H-pyrido[3',4':4,5]pyrrolo[2,3-g]isoquinolin-10-yl)-N,N-dimethyl-propane-1,3-diamine,
  N,N-diethyl-N'-(6-methyl-5H-pyrido[3',4':4,5]pyrrolo[2,3-g]isoquinoline-10-yl)-propane-1,3-diamine, and
  6-methyl-5H-pyrido[3',4':4,5]pyrrolo[2,3-g]isoquinolin-10-yl-amine.

6. The method of claim 1, wherein said splicing process is either constitutive or dependent on ESE, ISE, ESS or ISS regulatory sequences.

7. The method of claim 6, wherein said splicing process is either constitutive or dependent on ESE regulatory sequences.

8. The method of claim 1, wherein said medicine further comprises an excipient.

9. The method of claim 8, wherein said medicine is in a solid or liquid form.

10. 10-chloro-2,6-dimethyl-2H-pyrido[3',4':4,5]pyrrolo[2,3-g]isoquinoline.

11. N-ethyl-N-[3-(6-methyl-5H-pyrido[3',4':4,5]pyrrolo[2,3-g]isoquinolin-10-ylamino)-propyl]-succinamic acid.

12. A medicine comprising a compound as in any one of claims 10 and 11.

13. A medicine comprising a compound selected from the group consisting of:
10-chloro-2,6-dimethyl-2H-pyrido[3',4':4,5]pyrrolo[2,3-g]isoquinoline,
N'-(6,11-dimethyl-5H-pyrido[3',4':4,5]pyrrolo[2,3-g]isoquinolin-10-yl)-N,N-dimethyl-propane-1,3-diamine,
N,N-dimethyl-N'-(6-methyl-5H-pyrido[3',4':4,5]pyrrolo[2,3-g]isoquinolin-10-yl)-propane-1,3-diamine,
N-ethyl-N-[3-(6-methyl-5H-pyrido[3',4':4,5]pyrrolo[2,3-g]isoquinolin-10-ylamino)-propyl]-succinamic acid,
2-{(2-hydroxy-ethyl)-[3-(6-methyl-5H-pyrido[3',4':4,5]pyrrolo[2,3-g]isoquinolin-10-ylamino}propyl]-aminoethanol,
N-(6-methyl-5H-pyrido[3',4':4,5]pyrrolo[2,3-g]isoquinolin-10-yl)-propane-1,3-diamine,
N-3-(5,6-dimethyl-5H-pyrido[3',4':4,5]pyrrolo[2,3-g]isoquinolin-10-yl)-N,N-1-diethyl-butane-1,3-diamine,
N-(6,11-dimethyl-5H-pyrido[3',4':4,5]pyrrolo[2,3-g]isoquinolin-10-yl)-N'-ethyl-propane-1,3-diamine,
N'-(5,6-dimethyl-5H-pyrido[3',4':4,5]pyrrolo[2,3-g]isoquinolin-10-yl)-N,N-dimethyl-propane-1,3-diamine,
N-(5,6-dimethyl-5H-pyrido[3',4':4,5]pyrrolo[2,3-g]isoquinolin-10-yl)-N'-ethyl-propane-1,3-diamine,
(3-imidazol-1-yl-propyl)-(6-methyl-5H-pyrido[3',4':4,5]pyrrolo[2,3-g]isoquinolin-10-yl)-amine,
N-1,N-10-Bis-(3-diethylamino-propyl)-3,6-dimethyl-5H-pyrido[3',4':4,5]pyrrolo[2,3-g]isoquinoline-1,10-diamine,
N,N-dimethyl-N'-(10,11-dimethyl-10H-pyrido[3',4':4,5]pyrrolo[3,2-g]quinoline)4-yl-propane-1,3-diamine,
N,N-diethyl-N'-(10,11-dimethyl-10H-pyrido[3',4':4,5]pyrrolo[3,2-]quinoline)-4-yl-propane-1,3-diamine,
N,N-diethyl-N'-(11-methyl-10H-pyrido[3',4':4,5]pyrrolo[3,2-g]quinoline)-4-yl-propane-1,3-diamine,
N,N-dimethyl-N'-(11-methyl-10H-pyrido[3',4':4,5]pyrrolo[3,2-g]quinoline)-4-yl-propane-1,3-diamine,
N-(5,6-dimethyl-5H-pyrido[3',4':4,5]pyrrolo[2,3-g]isoquinolin-10-yl)-N'-ethyl-propane-1,3-diamine, and
6-methyl-5H-pyrido[3',4':4,5]pyrrolo[2,3-g]isoquinolin-10-yl-amine.

\* \* \* \* \*

UNITED STATES PATENT AND TRADEMARK OFFICE
CERTIFICATE OF CORRECTION

PATENT NO. : 7,989,467 B2  
APPLICATION NO. : 10/570849  
DATED : August 2, 2011  
INVENTOR(S) : Tazi et al.

Page 1 of 1

It is certified that error appears in the above-identified patent and that said Letters Patent is hereby corrected as shown below:

On the title page, Item [86] after § 371 (c)(1), (2), (4) Date: delete "Sep. 6, 2004" should read --Mar. 6, 2006--.

Signed and Sealed this  
Eighth Day of October, 2013

Teresa Stanek Rea  
*Deputy Director of the United States Patent and Trademark Office*